(12) United States Patent
Lewis et al.

(10) Patent No.: US 8,057,814 B2
(45) Date of Patent: *Nov. 15, 2011

(54) DRUG DELIVERY FROM STENTS

(75) Inventors: Andrew L. Lewis, Surrey (GB); Peter W. Stratford, Surrey (GB); Michael J. Driver, Surrey (GB)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/773,674

(22) Filed: May 4, 2010

(65) Prior Publication Data

US 2010/0222867 A1    Sep. 2, 2010

Related U.S. Application Data

(63) Continuation of application No. 10/466,153, filed as application No. PCT/GB02/00103 on Jan. 11, 2002, now Pat. No. 7,713,538.

(30) Foreign Application Priority Data

Jan. 11, 2001    (GB) .................................. 0100761.6

(51) Int. Cl.
*A61F 13/00*    (2006.01)

(52) U.S. Cl. ...................................................... 424/422

(58) Field of Classification Search .................. None
See application file for complete search history.

(56) References Cited

U.S. PATENT DOCUMENTS

| | | | |
|---|---|---|---|
| 5,240,958 A | | 8/1993 | Campion |
| 5,380,299 A | | 1/1995 | Fearnot et al. |
| 5,739,236 A | * | 4/1998 | Bowers et al. ............... 526/277 |
| 5,900,246 A | | 5/1999 | Lambert |
| 6,113,943 A | | 9/2000 | Okada et al. |
| 6,420,427 B1 | | 7/2002 | Takahashi et al. |
| 7,713,538 B2 | * | 5/2010 | Lewis et al. ................. 424/422 |
| 2002/0082685 A1 | | 6/2002 | Sirhan et al. |
| 2002/0155113 A1 | | 10/2002 | Chun et al. |
| 2003/0004141 A1 | | 1/2003 | Brown |
| 2003/0170287 A1 | | 9/2003 | Prescott |
| 2004/0152785 A1 | | 8/2004 | Okuyama et al. |

FOREIGN PATENT DOCUMENTS

| | | | |
|---|---|---|---|
| EP | 0623354 | | 11/1994 |
| EP | 0923953 | | 6/1999 |
| WO | WO 93/01221 | | 1/1993 |
| WO | WO 93/21942 | | 11/1993 |
| WO | WO 94/10990 | | 5/1994 |
| WO | WO 94/21309 | | 9/1994 |
| WO | WO 95/03036 | | 2/1995 |
| WO | WO 98/22162 | | 5/1998 |
| WO | WO 98/25597 | | 6/1998 |
| WO | WO 98/30615 | | 7/1998 |
| WO | WO 99/01118 | | 1/1999 |
| WO | WO 99/32150 | | 7/1999 |
| WO | WO 99/47138 | | 9/1999 |
| WO | WO 00/04892 | | 2/2000 |
| WO | WO 00/53210 | | 9/2000 |
| WO | WO 00/56283 | * | 9/2000 |
| WO | WO 01/01957 | | 1/2001 |

OTHER PUBLICATIONS

International Search Report for PCT/GB 02/00103, mailed May 13, 2002, 3 pgs.
Fischell "Polymer Coatings for Stents", Circulation vol. 94, No. 7, pp. 1494-1495 (1996).
Kalyanasundaram et al., "Environmental Effects on Vibronic Band Intensities in Pyrene Monomer Fluorescence and their Application in Studies of Micellar Systems", J. of the American Chem. Soc. vol. 99 (7), pp. 2039-2044 (1977).
McNair et al., "Drug Delivery from Novel PC Hydrogels", Proceed. Intern. Symp. Control. Rel. Bioact. Mat. 22, pp. 338-339 (1995).
Topol et al., "Frontiers in Interventional Cardiology", Circulation vol. 98, pp. 1802-1820 (1998).
Van der Giessen et al., "Marked Inflammatory Sequelae to Implantation of Biodegradable and Nonbiodegradable Polymers in Porcine Coronary Arteries", Circulation vol. 94, No. 7, pp. 1690-1697 (1996).

* cited by examiner

*Primary Examiner* — Robert A Wax
*Assistant Examiner* — Bethany Barham
(74) *Attorney, Agent, or Firm* — Squire, Sanders & Dempsey (US) LLP

(57) ABSTRACT

An intravascular stent has a coat comprising a crosslinked amphiphilic polymer and a sparingly water soluble matrix metalloproteinase inhibitor (MMPI). Preferably the polymer is formed from 2-methacryloyloxy-2'-ethyltrimethylammonium phosphate inner salt, $C_{4-18}$ alkyl methacrylate and reactive and/or crosslinking monomer and the MMPI is a hydroxamic acid, more preferably batimastat. Preclinical and clinical results are reported, showing good luminal areas and reduced intimal thickening.

34 Claims, 7 Drawing Sheets

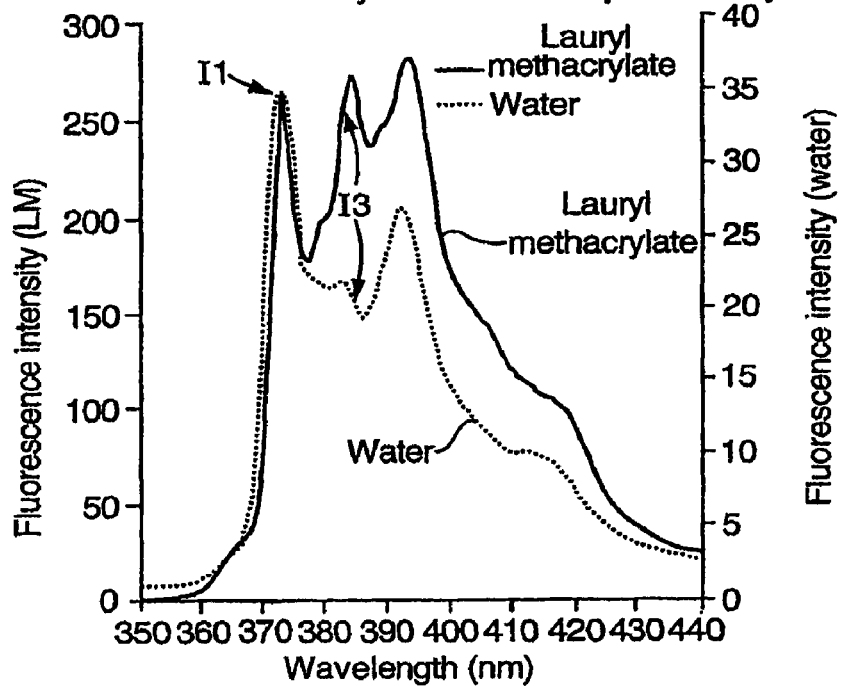
Fig.3.
I3/I1 ratios for different systems and lauryl methacrylate
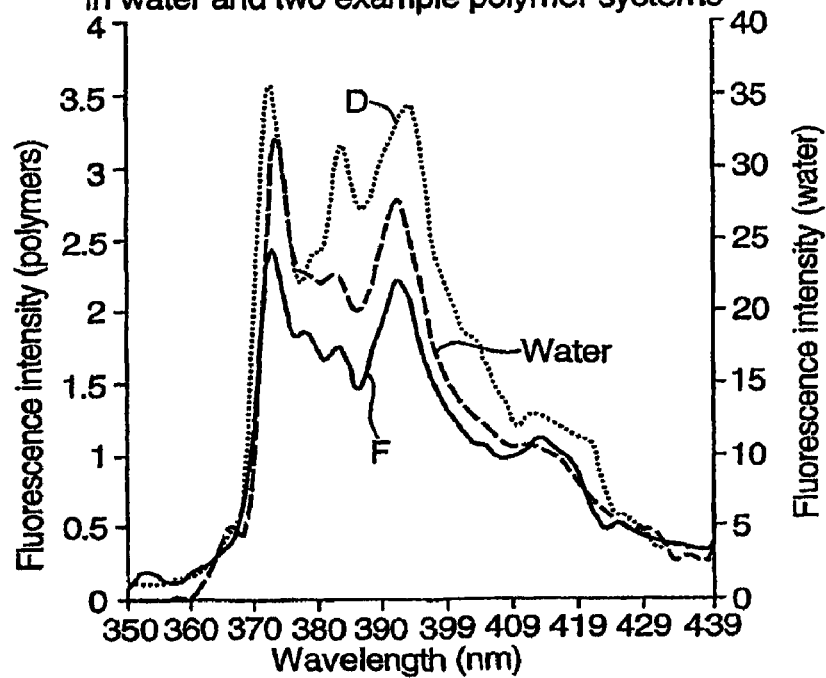
Fig.4. Comparison of fluorescence spectra of pyrene in water and two example polymer systems

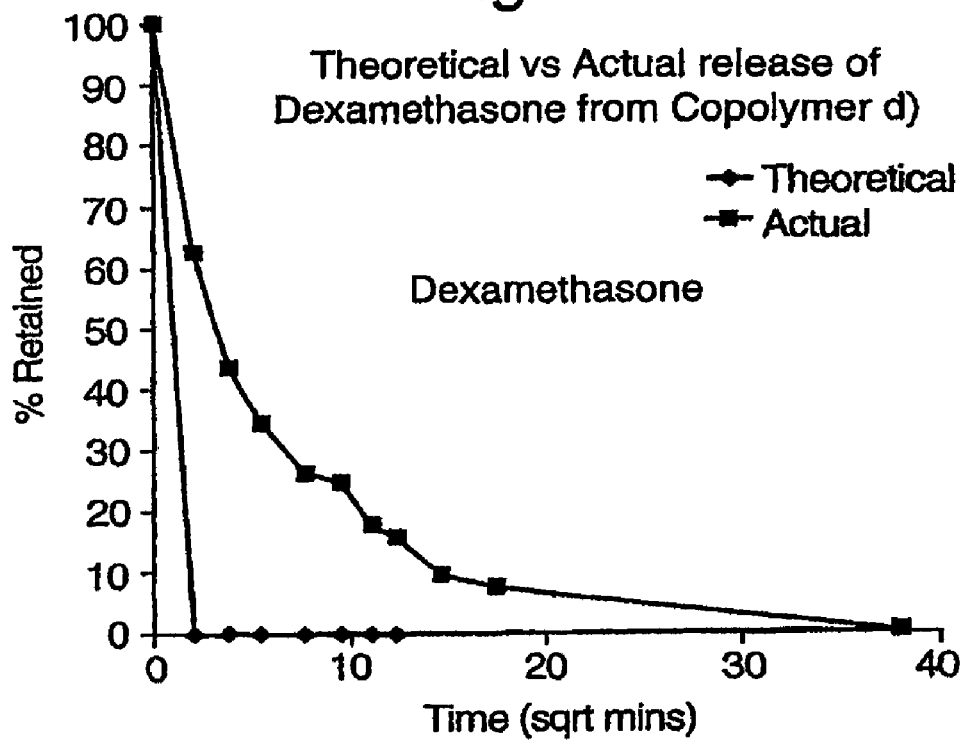
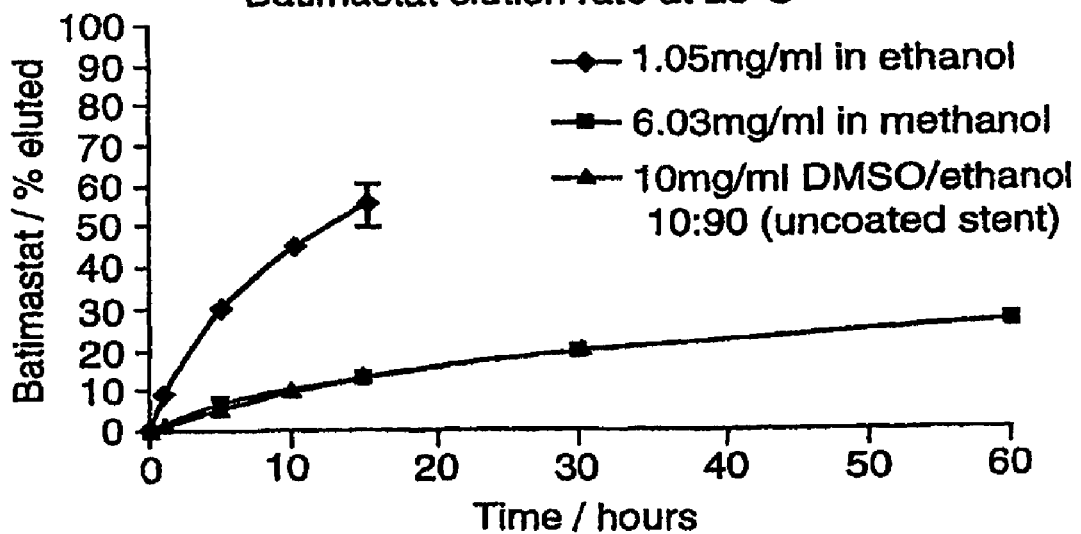

Comparison of batimastat delivered to a range of coronary artery vessel wall diameters.

Figure 8 - SEM: Control (unloaded stent):
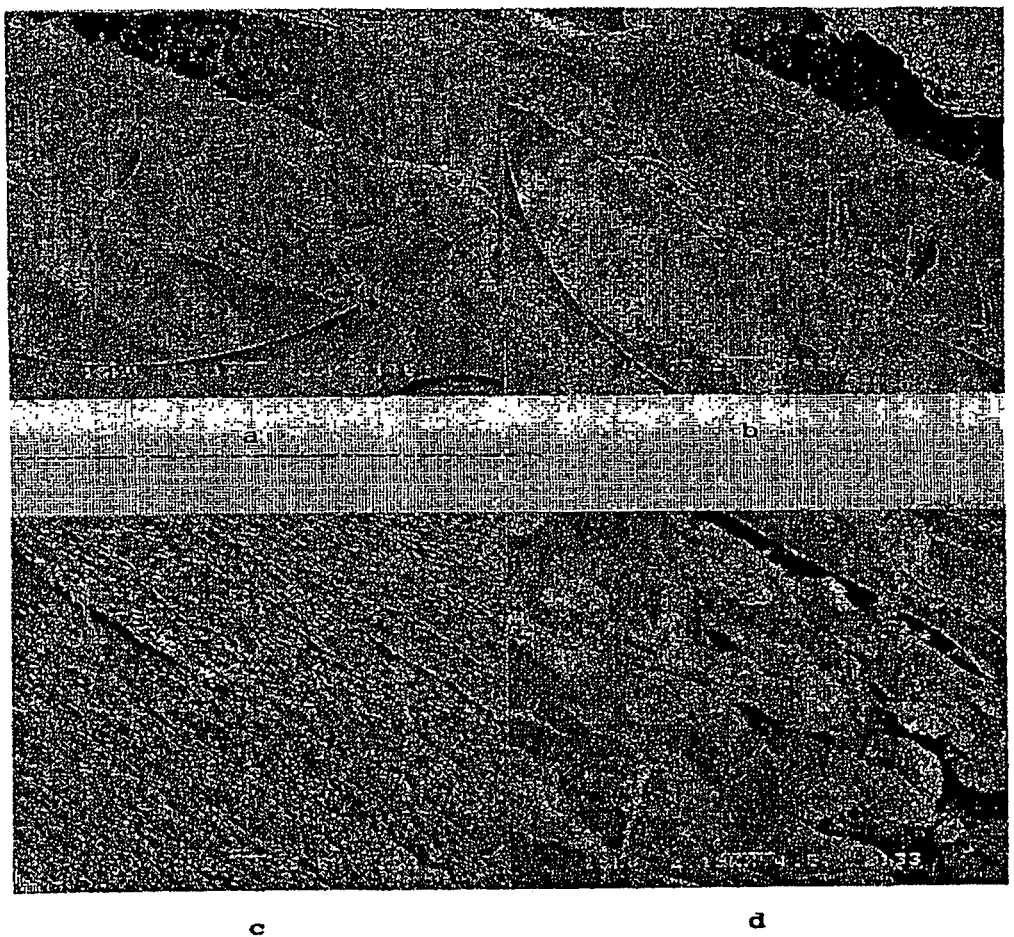

Figure 9 - SEM: Low dose stent:
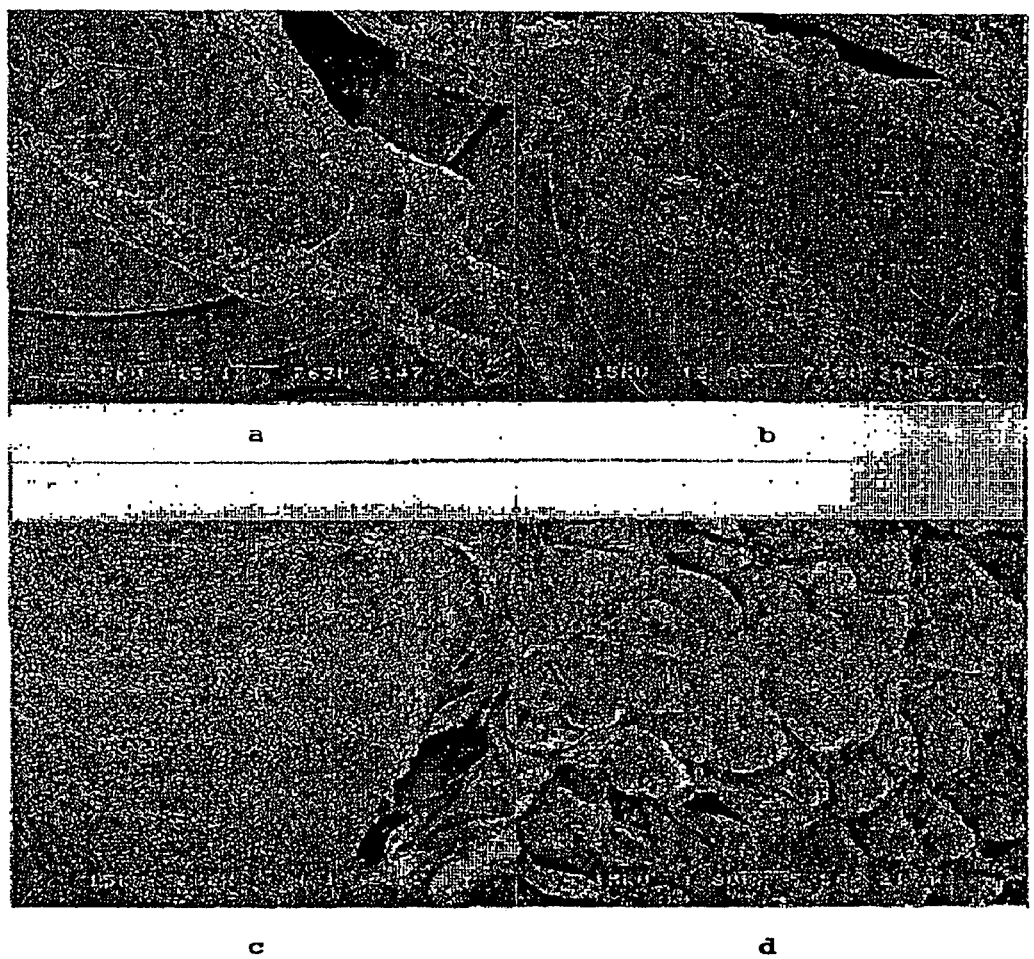

Figure 10 - SEM: High dose stent:
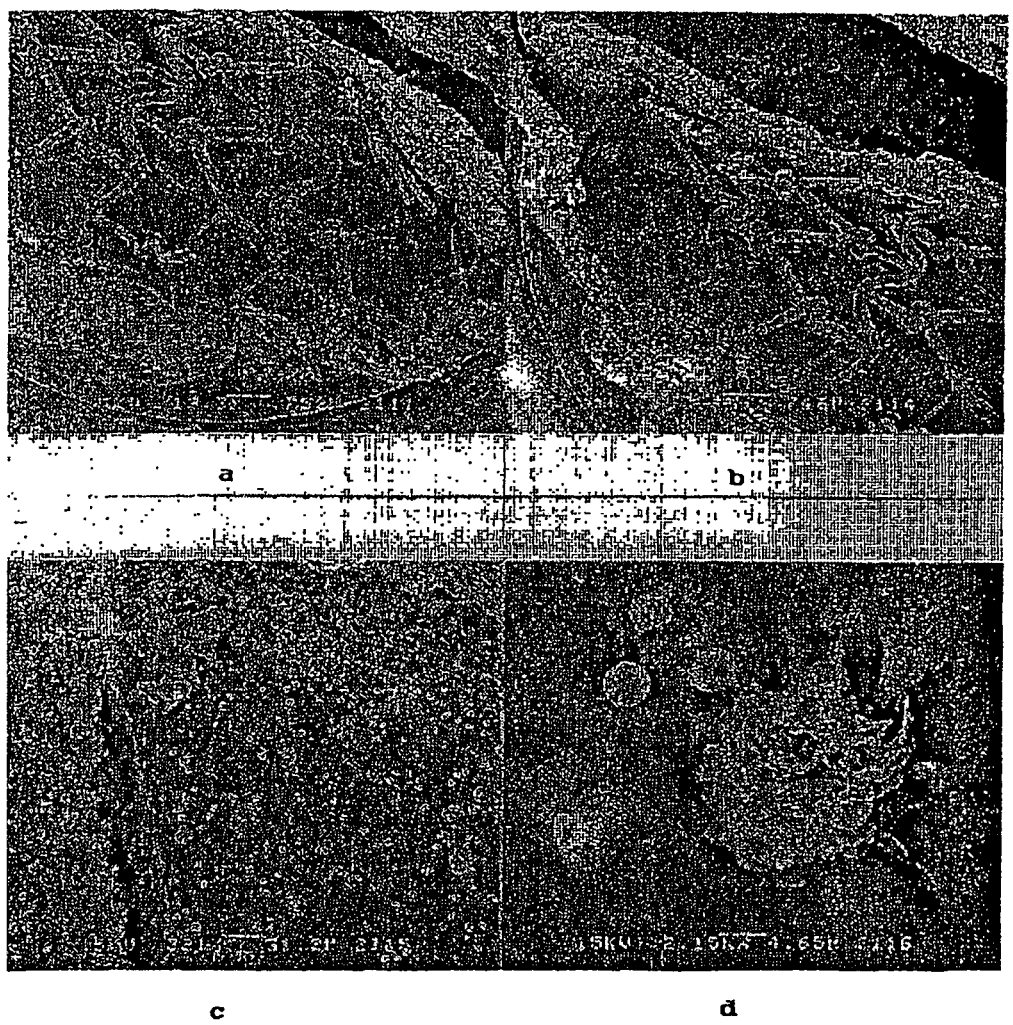

DRUG DELIVERY FROM STENTS

CROSS-REFERENCE TO RELATED APPLICATION

This is a continuation application of U.S. application Ser. No. 10/466,153, filed Jan. 7, 2004 now U.S. Pat. No. 7,713, 538, which is a U.S. national phase application PCT application No. PCT/GB02/00103, filed Jan. 11,2002 the teaching of which is incorporated herein in its entirety by reference.

BACKGROUND OF THE INVENTION

The present invention relates to the delivery of drugs from stents coated with polymer. In particular the invention relates to delivery of matrix metalloproteinase inhibitors, for inhibition of restenosis following stent implantation in the treatment of cardiovascular disease.

A leading cause of mortality within the developed world is cardiovascular disease. Coronary disease is of most concern. Patients having such disease usually have narrowing in one or more coronary arteries. One treatment is coronary stenting, which involves the placement of a stent at the site of acute artery closure. This type of surgery has proved effective in restoring vessel patency and decreasing myocardial ischemia. However the exposure of currently used metallic stents to flowing blood can result in thrombus formation, smooth muscle cell proliferation and acute thrombotic occlusion of the stent.

Non-thrombogenic and anti-thrombogenic coatings for stents have been developed. One type of balloon expandable stent has been coated with polymers having pendant zwitterionic groups, specifically phosphorylcholine (PC) groups, generally described in WO-A-93/01221. A particularly successful embodiment of those polymers suitable for use on balloon expandable stents has been described in WO-A-98/30615. The polymers coated onto the stent have pendant crosslinkable groups which are subsequently crosslinked by exposure to suitable conditions, generally heat and/or moisture. Specifically a trialkoxysilylalkyl group reacts with pendant groups of the same type and/or with hydroxyalkyl groups to generate intermolecular crosslinks. The coatings lead to reduced thrombogenicity.

Fischell, T. A. in Circulation (1996) 94:1494-1495 describes tests carried out on various polymer coated stents. A thinner uniform polyurethane coating, having a thickness of 23 μm was observed to have a better performance than a relatively non uniform thicker layer having a thickness in the range 75 to 125 μm. The thicker coatings are further described by Van der Giessen, W J et al. in Circulation: 1996: 94:1690-1697.

It has been suggested to utilise coatings on stents as reservoirs for pharmaceutically active agents desired for local delivery.

In U.S. Pat. No. 5,380,299 a stent is provided with a coating of a thrombolytic compound and optionally an outer layer of an anti-thrombotic compound. The stent may be precoated with a "primer" such as a cellulose ester or nitrate.

Other drug containing stents and stent coatings are described by Topol and Serruys in Circulation (1998) 98:1802-1820.

McNair et al., in Proceedings of the International Symposium on Controlled Release Bioactive Materials (1995) 338-339 describe in vitro investigations of release of three model drugs, caffeine, dicloxacillin and vitamin B12, from hydrogel polymers having pendant phosphorylcholine groups. Alteration of the hydrophilic/hydrophobic ratio of the (hydrophilic) phosphorylcholine monomer 2-methacryloyloxyethyl phosphorylcholine, (HEMA-PC) and a hydrophobic comonomer and crosslinking of the polymer allows preparation of polymers having water contents when swollen in the range 45 to 70 wt %. Crosslinking is achieved by incorporating a reactive monomer 3-chloro-2-hydroxypropylmethacrylate. The tests are carried out on membranes swollen in aqueous drug solutions at 37° C. The release rates of the model drugs are influenced by the molecular size, solute partitioning and degree of swelling of the polymer. Dicloxacillin is found to have a higher half life for release than its molecular size would indicate, and the release profile did not appear to be Fickian.

McNair et al., in Medical Device Technology, December 1996, 16-22, describe three series of experiments. In one, polymers formed of HEMA-PC and lauryl methacrylate crosslinked after coating by unspecified means are cocoated with drugs onto stents. Release rates of dexamethasone from the stent, apparently into an aqueous surrounding environment, was determined. Drug release from cast membranes, as model coatings, showed that the release rate obeyed Fickian diffusion principles, for hydrophilic solutes. In the third series of tests, a non-crosslinked polymer coating, free of drug, coated on a stent, had a significant decrease in platelet adhesion when coated on a stent used in an ex-vivo arteriovenous shunt experiment. The stent coating method was not described in detail.

Stratford et al in "Novel phosphorylcholine based hydrogel polymers: Developments in medical device coatings" describe polymers formed from 2-methacryloyloxyethyl phosphorylcholine, a higher alkyl methacrylate, hydroxypropylmethacrylate and a methacrylate ester comonomer having a reactive pendant group. These PC polymers were investigated to determine the feasibility of delivering drugs and model drugs. Results are shown for caffeine, dicloxacillin, vitamin B12, rhodamine and dipyridamole. The device on which the drug is coated is a guidewire that is, it is not an implant.

In EP-A-0623354, solutions of drug and polymer in a solvent were used to coat Wiktor type tantalum wire stents expanded on a 3.5 mm angioplasty balloon. The coating weights per stent were in the range 0.6 to 1.5 mg. Coating was either by dipping the stent in the solution, or by spraying the stent from an airbrush. In each case coating involved multiple coating steps. The drug was for delivery to the vessel wall. The drugs suggested as being useful for delivery from stents were glucocorticoids, antiplatelet agents, anticoagulants, antimitotic agents, antioxidants, antimetabolite agents and antiinflammatory agents. The worked examples all use dexamethasone delivered from a bioabsorbable polymer.

In U.S. Pat. No. 5,900,246 drugs are delivered from a polyurethane coated substrate such as a stent. The polyurethanes may be modified to control its compatibility with lipophilic or hydrophilic drugs. Suitable drugs are antithrombotic agents, antiinflammatory agents such as steroids, antioxidants, antiproliferative compounds and vasodilators. Particularly preferred drugs are lipophilic compounds. A polyurethane coated stent is contacted with a drug in a solvent which swells the polyurethane, whereby drug is absorbed into the polyurethane. Selection of a suitable solvent took into account the swellability of the polyurethane and the solubility of the drug in the solvent. It was observed that lipophilic drugs loaded in this way released more slowly from hydrophobic polymer than more hydrophilic drugs, by virtue of interaction of the lipophilic drug with hydrophobic polymer.

In EP-A-0923953 coatings for implantable devices, generally stents, comprise an undercoat comprising particulate drug and polymer matrix, and an overlying topcoat which partially covers the undercoat. The top coat must be discontinuous in situ, in order to allow release of the drug from the undercoat. Examples of drugs include antiproliferatives, steroidal and non steroidal antiinflammatories, agents that inhibit hyperplasia, in particular restenosis, smooth muscle cell inhibitors, growth factor inhibitors and cell adhesion promoters. The worked examples use heparin and dexamethasone. The polymer of the undercoat is, for example, hydrophobic biostable elastomeric material such as silicones, polyurethanes, ethylene vinyl acetate copolymers, polyolefin elastomers, polyamide elastomers and EPDM rubbers. The top layer is suitably formed of non-porous polymer such as fluorosilicones, polyethylene glycols, polysaccharides and phospholipids. In the examples, the undercoat comprised silicone polymer, and coating with the polymer/drug mixture was carried out by spraying a suspension in which both drug and polymer were dispersed, followed by curing of the polymer.

In our earlier specification WO-A-0101957, unpublished at the priority date hereof, we describe methods for loading drugs into polymer coated stents. The polymer coating preferably comprised a crosslinked copolymer of an ethylenically unsaturated zwitterionic monomer with a hydrophobic comonomer. The drug was intended to be delivered into the wall of the vessel in which the stent was implanted and the thickness of the coating on the stent was adapted so as to provide higher drug dosage on the outer surface of the stent. The drugs were selected from antiproliferatives, anticoagulants, vasodilators, antiinflammatories, cytotoxic agents and antiangiogenic compounds.

It is well known to those who work in the area of surfactant chemistry that it is possible to determine critical micelle concentrations by use of hydrophobic probes, which seek out the hydrophobic interior of micelles in preference to remaining in an aqueous environment. Pyrene is one such molecule. Moreover, the fluorescence intensities of various vibronic fine structures in the pyrene molecules' fluorescence spectrum shows strong environmental effects based upon the polarity of the solvent in which it is present (Kalyanasundaram, K. et al; JACC, 99(7), 2039, 1977). The ratio of the intensity of a pair of characteristic bonds (I3:I1) is relevant to the environment. A value for I3:I1 of about 0.63 is indicative of an aqueous environment whilst a value of about 1 is indicative of hydrophobic environment.

Matrix metalloproteinases (or matrix metalloproteases) MMPs are zinc-binding endopeptidases involved in connective tissue matrix remodelling and degradation of the extra cellular matrix (ECM), an essential step in tumour invasion, angiogenesis and metastasis. The MMP's each have different substrate specificities within the ECM and are important in its degradation. The analysis of MMP's in human mammary pathology showed that several MMP's are involved:collagenase (MMP1) which degrades fibrillar interstitial collagens; gelatinase (MMP2), which mainly degrade type IV collagen; stromelysin (MMP3) which has a wide range of substrate activities.

Tissue inhibitors of metalloproteinase (T1MPs) represent a family of ubiquitous proteins which are natural inhibitors of MMPIs. TIMP-4 is thought to function in a tissue-specific fashion in ECM hemostasis. WO-A-00/53210 suggests that TIMP-4 may be useful in the treatment of vascular diseases such as restenosis after balloon angioplasty. Local delivery of the TIMP-4, or oligonucleotide encoding TIMP-4 is suggested through injecting needles, or through a catheter used in an angioplasty intervention.

U.S. Pat. No. 5,240,958 describes a class of hydroxamic acid derivatives of oligopeptides which inhibit metalloproteinases that is are matrix metalloproteinase inhibitors, MMPIs. The compounds are useful in the management of disease involving tissue degradation, especially rheumatoid arthritis, or other arthropathies, inflammation, dermatological disease, bone resorption and tumour invasion, as well as promoting wound healing. Local delivery into a joint may be effected by direct injection. One of the exemplified compounds is batimastat. Hydroxamic acid MMP1's are shown to promote tumour regression or inhibit cancer cell proliferation in WO-A0-93/21942. In WO-A-94/10990 such compounds are shown to inhibit tumour necrosis factor (TNF) production.

In WO-A-98/25597 MMPI's are used to prevent and treat heart failure and ventricular dilation. In WO-A-99/47138, the use of MMPI's in combination with statins are used to treat vascular diseases, including inhibiting restenosis. The delivery of the MMPI is systemic, although release may be controlled. In WO-A-99/32150, MMPI's are used in combination with ACE inhibitors to slow and reverse the process of fibrosis, ventricular dilation and heart failure. In WO-A-00/04892 a combination of MMPI's and acyl-Co:Acholesterol acyltransferase (ACAT) are used to reduce smooth muscle cell (SMC) and macrophage proliferation in atherosclerotic legions.

In WO-A-95/03036 it is suggested that stents are coated with antiangiogenic drugs to inhibit tumour invasion. Examples of antiangiogenic drugs include TIMP-1, TIMP-2 and metalloproteinase inhibitors such as BB94 (batimastat). The antiangiogenic agent is delivered from a polymeric carrier.

In U.S. Pat. No. 6,113,943 it is suggested that batimastat is an angiogenesis suppressor. It is delivered in that invention from a lactic acid polymer by sustained release.

In WO-A-00/56283, polymers having metal chelating activities are said to have MMP inhibitory activity. The polymers may be coated onto a stent. It is suggested that MMP's contribute to the development of atherosclerotic plaques and post angioplasty restenotic plaques. The IVIMP inhibiting activity of the polymers is believed to be useful in inhibiting restenosis. The polymers may be coated onto a stent and may have additional pharmaceutically active agents dispersed therein, such as MMPI's, including hydroxamic acids and, specifically, batimastat. Polymers having MMPI activity are capable of chelating divalent metals, and are generally polymers of unsaturated carboxylic acids although sulphonated anionic hydrogels may be used. One example of a monomer for forming a sulphonated anionic hydrogel is N,N-dimethyl-N-methacryloyloxyethyl-N-(3-sulphopropyl) ammonium betaine. Other examples of polymers are acrylic acid based polymers modified with $C_{10-30}$-alkyl acrylates crosslinked with di- or higher-functional ethylenically unsaturated crosslinking agents. There is no specific suggestion of how to provide a coating on a stent comprising both MMPI active polymer and additional therapeutic agent.

In WO-A-99/01118, antioxidants are combined with antineoplastic drugs to improve their cytotoxicity. One example of the antineoplastic drug whose activity may be increased is batimastat. One utility of the antineoplastic combination is in the treatment of vascular disease. The drug combination may be administered from a controlled release system.

The crosslinkable polymer of 2-methacryloyloxyethyl-2'-trimethyl ammoniumethylphosphate inner salt and dodecyl methacrylate with crosslinking monomer, coated onto a stent and cured, has been shown to reduce restenosis following stent delivery for the treatment of atherosclerotic conditions.

In WO-A-01/01957 mentioned above, we show that a range of drugs may be loaded onto the polymer coated stents such that delivery of the drug into adjacent tissue takes place.

SUMMARY OF THE INVENTION

The present invention relates to a stent having a polymer coating, and comprising a sparingly water soluble matrix metalloproteinase inhibitor which may be delivered over an extended period of time from the stents after placement.

A new intravascular stent comprises a metal body having a coating comprising polymer and a restenosis inhibiting agent in which the restenosis inhibiting agent is a sparingly water soluble matrix metalloproteinase inhibitor (MMPI) and the polymer in the coating is a crosslinked amphiphilic polymer.

Preferably, on at least the outer wall of the stent the coating comprises a layer of the said amphiphilic polymer in which the MMPI is absorbed. Additionally there may be MMPI absorbed into polymer in the coating on the inner wall.

It may be possible to provide a sufficiently high does of MMPI on the stent in form of absorbed material. However, sometimes it may be desirable to provide higher doses than may be loaded into the amphiphilic polymer matrix. For instance, it may be undesirable to increase the level of polymer on the stent so as to be able to support a higher loading of MMPI. In a preferred stent, the coating on the outer wall of the stent comprises an inner layer of the said amphiphilic polymer, and, adhered to said inner layer, crystalline MMPI. Provision of crystalline MMPI may also confer useful release characteristics on the stent. The crystalline material may be controlled of a particle size, for instance, to confer desired release characteristics which complement the release of absorbed drug from the polymer coating.

In a preferred embodiment of the invention, the coating on at least the outer wall of the stent comprises an inner layer of the said amphiphilic polymer and the top coat comprising a non-biodegradable, biocompatible semipermeable polymer. The semipermeable polymer is selected so as to allow permeation of MMPI through the top layer when the stent is in an aqueous environment. In such an environment, the semipermeable polymer may, for instance, be swollen, and it is in this form that it should allow permeation of the active MMPI. A topcoat may confer desirable controlled release characteristics. Its use is of particular value for the preferred embodiment where coating comprises crystalline MMPI adhered to an inner layer of amphiphilic polymer. The topcoat in such an embodiment has several functions. It provides a smooth outer profile, minimises loss of MMPI during delivery, provides a biocompatible interface with the blood vessel after implantation and controls release of MMPI from the stent into the surrounding tissue in use.

A topcoat is preferably substantially free of MMPI prior to implantation of the stent.

A topcoat is preferably formed of a second cross-linked amphiphilic polymer. The second amphiphilic polymer may be the same as the first amphiphilic polymer.

In the present invention, an amphiphilic polymer comprises groups conferring hydrophilicity and groups conferring hydrophobicity. Preferably the groups conferring hydrophilicity comprise zwitterionic groups.

Preferably the polymer in the coating, when swollen with water containing pyrene, has hydrophobic domains observable by pyrene fluorescence intensity ratio I3:I1 of at least 0.8, preferably about 1.

Preferably the groups conferring hydrophobicity comprise pendant hydrophobic groups selected from $C_{4-24}$-alkyl, -alkenyl and -alkynyl groups any of which may be substituted by one or more fluorine atoms, aryl, $C_{7-24}$ aralkyl, oligo ($C_{3-4}$ alkoxy) alkyl and siloxane groups.

Most preferably the polymer is formed from ethylenically unsaturated monomers including a zwitterionic monomer and a hydrophobic comonomer. For forming a crosslinkable polymer, the ethylenically unsaturated monomers preferably include one or more reactive monomer having a pendant reactive group(s) capable of forming intermolecular crosslinks.

Preferably the zwitterionic monomer has the general formula I:

$$YBX \qquad \qquad I$$

wherein

B is a straight or branched alkylene (alkanediyl), alkyleneoxaalkylene or alkylene oligo-oxaalkylene chain optionally containing one or more fluorine atoms up to and including perfluorinated chains or, if X or Y contains a terminal carbon atom bonded to B, a valence bond;

X is a zwitterionic group; and

Y is an ethylenically unsaturated polymerisable group selected from

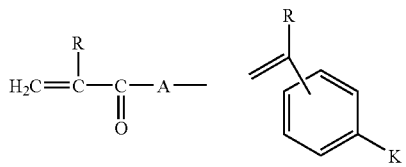

$CH_2$=$C(R)CH_2O$—, $CH_2$=$C(R)CH_2OC(O)$—, $CH_2$=$C(R)OC(O)$—, $CH_2$=$C(R)O$—, $CH_2$=$C(R)CH_2OC(O)N(R^1)$—, $R^2OOCCR$=$CRC(O)O$—, $RCH$=$CHC(O)O$—, $RCH$=$C(COOR^2)CH_2C(O)O$—,

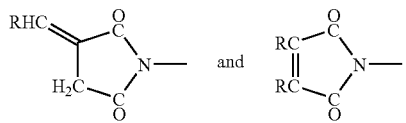

wherein:

R is hydrogen or a $C_1$-$C_4$ alkyl group;

$R^1$ is hydrogen or a $C_1$-$C_4$ alkyl group or $R^1$ is —B—X where B and X are as defined above; and $R^2$ is hydrogen or a $C_{1-4}$ alkyl group;

A is —O— or —$NR^1$—;

K is a group —$(CH_2)_pOC(O)$—, —$(CH_2)_pC(O)O$—, —$(CH_2)$, $OC(O)O$—, —$(CH_2)_pNR^3$—, —$(CH_2)_pNR^3C(O)$—, —$(CH_2)_pC(O)NR^3$—, —$(CH_2)_pNR^3C(O)O$—, —$(CH_2)_pOC(O)NR^3$—, —$(CH_2)_pNR^3C(O)NR^3$— (in which the groups $R^3$ are the same or different), —$(CH_2)_pO$—, —$(CH_2)_pSO_3$—, or, optionally in combination with B, a valence bond p is from 1 to 12; and $R^3$ is hydrogen or a $C_1$-$C_4$, alkyl group.

In group X, the atom bearing the cationic charge and the atom bearing the anionic charge are generally separated by 2 to 12 atoms, preferably 2 to 8 atoms, more preferably 3 to 6 atoms, generally including at least 2 carbon atoms.

Preferably the cationic group in zwitterionic group X is an amine group, preferably a tertiary amine or, more preferably, a quaternary ammonium group. The anionic group in X may be a carboxylate, sulphate, sulphonate, phosphonate, or more preferably, phosphate group. Preferably the zwitterionic group has a single monovalently charged anionic moiety and a single monovalently charged cationic moiety. A phosphate group is preferably in the form of a diester.

Preferably, in a pendant group X, the anion is closer to the polymer backbone than the cation.

Alternatively group X may be a betaine group (i.e. in which the cation is closer to the backbone), for instance a sulpho-, carboxy- or phosphor-betaine. A betaine group should have no overall charge and is preferably therefore a carboxy- or sulpho-betaine. If it is a phosphobetaine, the phosphate terminal group must be a diester, i.e., be esterified with an alcohol. Such groups may be represented by the general formula II $$-X^1-R^4-N^+(R^5)_2-R^6-V \qquad \text{II}$$

in which $X^1$ is a valence bond, —O—, —S— or —NH—, preferably —O—;

V is a carboxylate, sulphonate or phosphate (diester-monovalently charged) anion;

$R^4$ is a valence bond (together with $X^1$) or alkylene —C(O) alkylene- or —C(O)NHalkylene preferably alkylene and preferably containing from 1 to 6 carbon atoms in the alkylene chain;

the groups $R^5$ are the same or different and each is hydrogen or alkyl of 1 to 4 carbon atoms or the groups $R^5$ together with the nitrogen to which they are attached form a heterocyclic ring of 5 to 7 atoms; and $R^6$ is alkylene of 1 to 20, preferably 1 to 10, more preferably 1 to 6 carbon atoms.

One preferred sulphobetaine monomer has the formula III

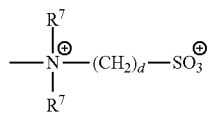

where the groups $R^7$ are the same or different and each is hydrogen or $C_{1-4}$ alkyl and d is from 2 to 4.

Preferably the groups $R^7$ are the same. It is also preferable that at least one of the groups $R^7$ is methyl, and more preferable that the groups $R^7$ are both methyl.

Preferably d is 2 or 3, more preferably 3.

Alternatively the group X may be an amino acid moiety in which the alpha carbon atom (to which an amine group and the carboxylic acid group are attached) is joined through a linker group to the backbone of polymer A. Such groups may be represented by the general formula IV

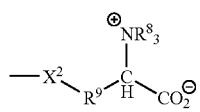

in which $X^2$ is a valence bond, —O—, —S— or —NH—, preferably —O—, $R^9$ is a valence bond (optionally together with $X^2$) or alkylene, —C(O)alkylene- or —C(O)NHalkylene, preferably alkylene and preferably containing from 1 to 6 carbon atoms; and the groups $R^8$ are the same or different and each is hydrogen or alkyl of 1 to 4 carbon atoms, preferably methyl, or two of the groups $R^8$, together with the nitrogen to which they are attached, form a heterocyclic ring of from 5 to 7 atoms, or the three group $R^8$ together with the nitrogen atom to which they are attached form a fused ring structure containing from 5 to 7 atoms in each ring.

X is preferably of formula V

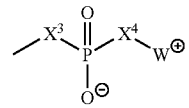

in which the moieties $X^3$ and $X^4$, which are the same or different, are —O—, —S—, —NH— or a valence bond, preferably —O—, and W+ is a group comprising an ammonium, phosphonium or sulphonium cationic group and a group linking the anionic and cationic moieties which is preferably a $C_{1-12}$ alkanediyl group.

Preferably W contains as cationic group an ammonium group, more preferably a quaternary ammonium group.

The group $W^+$ may for example be a group of formula

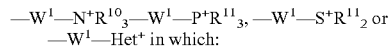

$W^1$ is alkanediyl of 1 or more, preferably 2-6 carbon atoms optionally containing one or more ethylenically unsaturated double or triple bonds, disubstituted-aryl, alkylene aryl, aryl alkylene, or alkylene aryl alkylene, disubstituted cycloalkyl, alkylene cycloalkyl, cycloalkyl alkylene or alkylene cycloalkyl alkylene, which group $W^1$ optionally contains one or more fluorine substituents and/or one or more functional groups; and either the groups $R^{10}$ are the same or different and each is hydrogen or alkyl of 1 to 4 carbon atoms, preferably methyl, or aryl, such as phenyl or two of the groups $R^{10}$ together with the nitrogen atom to which they are attached form a heterocyclic ring containing from 5 to 7 atoms or the three groups R together with the nitrogen atom to which they are attached form a fused ring structure containing from 5 to 7 atoms in each ring, and optionally one or more of the groups $R^{10}$ is substituted by a hydrophilic functional group, and the groups $R^{11}$ are the same or different and each is $R^{10}$ or a group $OR^{10}$, where $R^{10}$ is as defined above; or Het is an aromatic nitrogen-, phosphorus- or sulphur-, preferably nitrogen-, containing ring, for example pyridine.

Preferably $W^1$ is a straight-chain alkanediyl group, most preferably ethane-1,2-diyl.

Preferred groups X of the formula V are groups of formula VI:

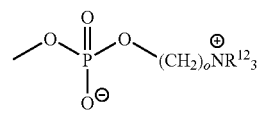

where the groups $R^{12}$ are the same or different and each is hydrogen or $C_{1-4}$ alkyl, and e is from 1 to 4.

Preferably the groups $R^{12}$ are the same. It is also preferable that at least one of the groups $R^{12}$ is methyl, and more preferable that the groups $R^{12}$ are all methyl.

Preferably e is 2 or 3, more preferably 2.

Alternatively the ammonium phosphate ester group VIII may be replaced by a glycerol derivative of the formula VB, VC or VD defined in our earlier publication no WO-A-93/01221.

Preferably the hydrophobic comonomer has the general formula VII $$Y^1 R^{13} \quad \text{VII}$$

wherein $Y^1$ is selected from

[structures: $H_2C=C(R^{14})-C(O)-A^1-$ and vinyl-substituted phenyl with $K^1-$]

$CH_2=C(R^{14})CH_2O-$, $CH_2=C(R^{14})CH_2OC(O)-$, $CH_2=C(R^{14})OC(O)-$,
$CH_2=C(R^{14})O-$, $CH_2=C(R^{14})CH_2OC(O)N(R^{15})-$,
$R^{16}OOCCR^{14}=CR^{14}C(O)O-$,
$R^{14}-CH=CHC(O)O-$, $R^{14}CH=C(COOR^{16})CH_2C(O)-O-$,

[two cyclic structures with $R^{14}HC=$ and $R^{14}C=$ groups containing N and C=O]

wherein:
$R^{14}$ is hydrogen or a $C_1$-$C_4$ alkyl group;
$R^{15}$ is hydrogen or a $C_1$-$C_4$ alkyl group or $R^{15}$ is $R^{13}$;
$R^{16}$ is hydrogen or a $C_{1-4}$ alkyl group;
$A^1$ is $-O-$ or $-NR^{15}-$; and
$K^1$ is a group $-(CH_2)_qOC(O)-$, $-(CH_2)_qC(O)O-$, $-(CH_2)_qOC(O)O-$,
$-(CH_2)_qNR^{17}-$, $-(CH_2)_qNR^{17}C(O)-$, $-(CH_2)_qC(O)NR^{17}-$, $-(CH_2)_qNR^{17}C(O)O-$,
$-(CH_2)_qOC(O)NR^{17}-$, $-(CH_2)_qNR^{17}C(O)NR^{17}-$ (in which the groups $R^{17}$ are the same or different), $-(CH_2)_qO-$, $-(CH_2)_qSO_3-$, or a valence bond
p is from 1 to 12;
and $R^{17}$ is hydrogen or a $C_1$-$C_4$ alkyl group;
and $R_{13}$ is the hydrophobic group.

In the comonomer of the general formula VII, the group $R^{13}$ is preferably a hydrophobic group, preferably:
a) a straight or branched alkyl, alkoxyalkyl or oligoalkoxyalkyl chain containing 4 or more, preferably 6 to 24 carbon atoms, unsubstituted or substituted by one or more fluorine atoms optionally containing one or more carbon double or triple bonds; or
b) a siloxane group $-(CR^{18}_2)_{qq}(SiR^{19}_2)(OSiR^{18}_2)_{pp}R^{19}$ in which each group $R^{18}$ is the same or different and is hydrogen or alkyl of 1 to 4 carbon atoms, or aralkyl, for example benzyl or phenethyl, each group $R^{19}$ is alkyl of 1 to 4 carbon atoms, qq is from 1 to 6 and pp is from 0 to 49

Most preferably $R^{13}$ is a straight alkyl having 4 to 18, preferably 12 to 16 carbon atoms.

The reactive monomer to which provides crosslinkability preferably has the general formula VIII $$Y^2 B^2 R^{20} \quad \text{VIII}$$

wherein
$B^2$ is a straight or branched alkylene, oxaalkylene or oligo-oxaalkylene chain optionally containing one or more fluorine atoms up to and including perfluorinated chains, or $B^2$ is a valence bond;

$Y^2$ is an ethylenically unsaturated polymerisable group selected from

[structures: $H_2C=C(R^{21})-C(O)-A^2-$ and vinyl-substituted phenyl with $K^2-$]

$CH_2=C(R^{21})CH_2-O-$, $CH_2=C(R^{21})CH_2OC(O)-$, $CH_2=C(R^{21})OC(O)-$,
$CH_2=C(R^{21})O-$, $CH_2=C(R^{21})CH_2OC(O)N(R^{22})-$, $R^{23}OOCCR^{21}=CR^{21}C(O)O-$,
$R^{21}H=CHC(O)O-$, $R^{21}H=C(COOR^{23})CH_2C(O)O-$

[two cyclic structures with $HR^{21}HC=$ and $R^{21}C=$ groups containing N and C=O]

where $R^{21}$ is hydrogen or $C_1$-$C_4$ alkyl;
$R^{23}$ is hydrogen, or $C_{1-4}$-alkyl group;
$A^2$ is $-O-$ or $-NR^{22}-$;
$R^{22}$ is hydrogen or a $C_1$-$C_4$ alkyl, group or $R^{22}$ is a group $B^2R^{20}$; p $K^2$ is a group $-(CH_2)_kOC(O)-$, $-(CH)_kC(O)O-$, $-(CH_2)_kOC(O)O-$,
$-(CH_2)_kNR^{22}-$, $-(CH_2)_kNR^{22}C(O)-$, $-(CH_2)_kOC(O)O-$, $-(CH_2)_kNR^{22}-$,
$-(CH_2)_kNR^{22}C(O)-$, $-(CH_2)_kC(O)NR^{22}-$, $-(CH_2)_kNR^{22}C(O)O-$, $-(CH_2)_kOC(O)NR^{22}-$, $-(CH_2)_kNR^{22}C(O)NR^{22}-$ (in which the groups $R^{22}$ are the same or different), $-(CH_2)_kO-$, $-(CH_2)_kSO_3-$, a valence bond and k is from 1 to 12; and
$R^{20}$ is a cross-linkable group.

Group $R^{20}$ is selected so as to be reactive with itself or with a functional group in the polymer (e.g. in group $R^{13}$) or at a surface to be coated. The group $R^{20}$ is preferably a reactive group selected from the group consisting of ethylenically and acetylenically unsaturated group containing radicals; aldehyde groups; silane and siloxane groups containing one or more substituents selected from halogen atoms and $C_{1-4}$-alkoxy groups; hydroxyl; amino; carboxyl; epoxy; $-CHOHCH_2Hal$ (in which Hal is selected from chlorine, bromine and iodine atoms); succinimido; tosylate; triflate; imidazole carbonyl amino; optionally substituted triazine groups; acetoxy; mesylate; carbonyl di(cyclo)alkyl carbodiimidoyl; isocyanate, acetoacetoxy; and oximino. Most preferably $R^{20}$ comprises a silane group containing at least one, preferably three substituents selected from halogen atoms and $C_{1-4}$-alkoxy groups, preferably containing three methoxy groups.

Preferably each of the groups Y to $Y^2$ is represented by the same type of group, most preferably each being an acrylic type group, of the formula $H_2C=C(R)C(O)-A$, $H_2C=C(R^{14})C(O)A^1$ or $H_2C=C(R^{21})O(O)-A^2$, respectively.

Preferably the groups R, $R^{14}$ and $R^{21}$ are all the same and are preferably H or, more preferably, $CH_3$. Preferably A, $A^1$ and $A^2$ are the same and are most preferably $-O-$. B and $B^2$ are preferably straight chain $C_{2-8}$-alkanediyl.

Preferably the ethylenically unsaturated comonomers comprise diluent comonomers which may be used to give the polymer desired physical and mechanical properties. Particular examples of diluent comonomers include alkyl(alk)acrylate preferably containing 1 to 24 carbon atoms in the alkyl group of the ester moiety, such as methyl (alk)acrylate or dodecyl methacrylate; a dialkylamino alkyl(alk)acrylate, preferably containing 1 to 4 carbon atoms in each alkyl moiety of the amine and 1 to 4 carbon atoms in the alkylene chain, e.g. 2-(dimethylamino)ethyl (alk)acrylate; an alkyl (alk)acrylamide preferably containing I to 4 carbon atoms in the alkyl group of the amide moiety; a hydroxyalkyl (alk)acrylate preferably containing from 1 to 4 carbon atoms in the hydroxyalkyl moiety, e.g. a 2-hydroxyethyl (alk)acrylate glycerylmonomethacrylate or polyethyleneglycol monomethacrylate; or a vinyl monomer such as an N-vinyl lactam, preferably containing from 5 to 7 atoms in the lactam ring, for instance vinyl pyrrolidone; styrene or a styrene derivative which for example is substituted on the phenyl ring by one or more alkyl groups containing from 1 to 6, preferably 1 to 4, carbon atoms, and/or by one or more halogen, such as fluorine atoms, e.g. (pentafluorophenyl)styrene.

Other suitable diluent comonomers include polyhydroxyl, for example sugar, (alk)acrylates and (alk)acrylamides in which the alkyl group contains from 1 to 4 carbon atoms, e.g. sugar acrylates, methacrylates, ethacrylates, acrylamides, methacrylamides and ethacrylamides. Suitable sugars include glucose and sorbitol. Diluent comonomers include methacryloyl glucose and sorbitol methacrylate.

Further diluents which may be mentioned specifically include polymerisable alkenes, preferably of 2-4 carbon atoms, eg. ethylene, dienes such as butadiene, ethylenically unsaturated dibasic acid anhydrides such as maleic anhydride and cyano-substituted-alkenes, such as acrylonitrile.

Particularly preferred diluent monomers are nonionic monomers, most preferably alkyl(alk)acrylates or hydroxyalkyl(alk)acrylates.

It is particularly desirable to include hydroxyalkyl(alk)acrylates in combination with reactive comonomers which contain reactive silyl moieties including one or more halogen or alkoxy substituent. The hydroxyalkyl group containing monomer may be considered a reactive monomer although it also acts as a diluent. Such reactive silyl groups are reactive with hydroxy groups to provide crosslinking of the polymer after coating, for instance.

A particularly preferred combination of reactive monomers is ω(trialkoxysilyl)alkyl(meth)acrylate and an ω-hydroxyalkyl(meth)acrylate.

The monomers may, in some embodiments, comprise an ionic comonomer. Suitable comonomers are disclosed in our earlier publication WO-A-9301221.

Preferably the zwitterionic monomer is used in the monomer mixture in a molar proportion of at least 1%, preferably less than 75%, more preferably in the range 5 to 50%, most preferably 10-33%. The hydrophobic comonomer is generally used in molar proportion of at least 2%, preferably at least 5% or at least 10%, more preferably in the range 15 to 99%, especially 50 to 95%, more especially 60 to 90%. The cross-linkable monomer is preferably used in a molar amount in the range 2 to 33%, preferably 3 to 20%, more preferably 5 to 10% by mole.

The zwitterionic polymer can be represented by the general formula IX:

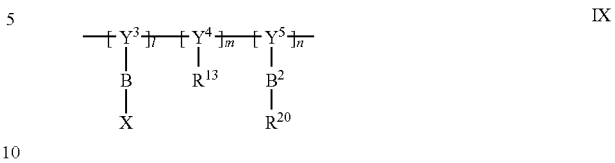

in which I is 1 to 75, m is 0 to 99, n is 0 to 33 and m+n is 25 to 99, $Y^3$ to $Y^5$ are the groups derived from Y to $Y^2$, respectively, of the radical initiated addition polymerisation of the ethylenic group in Y to $Y^2$, and B and X are as defined for the general formula I,
$R^{13}$ is as defined for the general formula VII, and
$B^2$ and $R^{20}$ are as defined for the general formula VIII.

In the preferred zwitterionic polymer in which Y, $Y^1$ and $Y^2$ are each acrylic groups the polymer has the general formula X

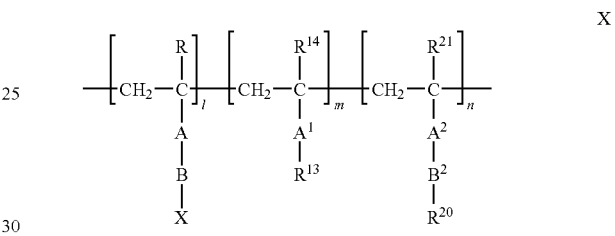

in which B, X, R and A are as defined for the compound of the general formula I, $R^{14}$, $A^1$ and $R^{13}$ are as defined for the general formula VII, $R^{21}$, $D^2$, $B^2$ and $R^{20}$ are as defined for the general formula VIII and I, m and n are as defined for the general formula IX The polymerisation is carried out using suitable conditions as known in the art. Thus the polymerisation involves radical initiation, using thermal or redox initiators which generate free radicals and/or actinic (e.g. u.v or gamma) radiation, optionally in combination with photoinitiators and/or catalysts. The initiator is preferably used in an amount in the range 0.05 to 5% by weight based on the weight of monomer preferably an amount in the range 0.1 to 3%, most preferably in the range 0.5 to 2%. The level of initiator is generally higher where the monomer includes reactive monomer and the polymer is cross-linkable, e.g. 1 to 20%.

The molecular weight of the polymer (as coated, where the polymer is cross-linkable) is in the range $1 \times 10^4$ to $10^6$ Da, preferably in the range $5 \times 10^4$ to $5 \times 10^5$ Da.

The monomer mixture may include a non-polymerisable diluent, for instance a polymerisation solvent. Such a solvent may provide solubility and miscibility of the monomers. The solvent may be aqueous or non-aqueous. The polymer may be recovered by precipitation from the polymerization mixture using a precipitating solvent, or recovery may involve removal of any non-polymerisable diluent by evaporation, for instance.

In the present invention the term sparingly water soluble means that at room temperature the solubility of the compound in water is less than 1 ml. The restenosis inhibiting agent is preferably a compound having a log P, where P is the octanol/water partition coefficient, of at least 1.5 for instance more than 2.

The MMPI used in the present invention is preferably a hydroxamic acid based collagenase inhibitor which is an oligopeptide compound, preferably of the general formula XI

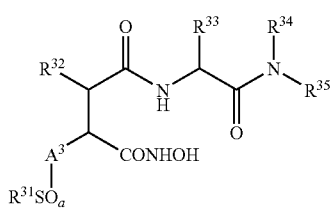

(XI)

wherein:

$R^{31}$ represents a hydrogen atom $C_{1-6}$ alkyl, phenyl, thienyl, substituted phenyl, phenyl($C_{1-6}$)alkyl, heterocyclyl, ($C_{1-6}$) alkylcarbonyl, phenacyl or substituted phenacyl group; or when a=0, $R^{31}$ represents $R^x$, wherein $R^x$ represents a group:

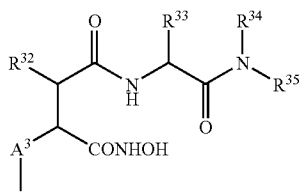

$R^{32}$ represents a hydrogen atom or a $C_{1-6}$ alkyl, $C_{1-6}$ alkenyl, phenyl($C_{1-8}$) alkyl, cycloalkyl(—$C_{1-6}$)alkyl or cycloalkenyl($C_{1-6}$)alkyl group;

$R^{33}$ represents an amino acid side chain or a $C_{1-6}$ alkyl, benzyl, ($C_{1-6}$ alkoxy)benzyl, benzyloxy($C_{1-6}$ alkyl) or benzyloxbenzyl group;

$R^{34}$ represents a hydrogen atom or a methyl group;

a is an integer having the value 0, 1 or 2; and $A^3$ represents a $C_{1-6}$ hydrocarbon chain, optionally substituted with one or more $C_{1-6}$ alkyl, phenyl or substituted phenyl groups;

or a salt thereof.

The term "amino acid side chain" means a characteristic side chain attached to the —CH(NH$_2$)(COOH) moiety in the following R or S amino acids: glycine, alanine, valine, leucine, isoleucine, phenylalanine, tyrosine, tryptophan, serine, threonine, cysteine, methionine, asparagine, glutamine, lysine, histidine, arginine, glutamic acid and aspartic acid.

There are several chiral centres in the MMPI compounds because of the present of asymmetric carbon atoms. The presence of several asymmetric carbon atoms gives rise to a number of diastereomers with the appropriate R or S stereochemistry at each chiral centre. General formula XI and, where appropriate, all other MMPI formulae in this specification are to be understood to include all such stereoisomers and mixtures (for example racemic mixtures) thereof. Compounds in which the chiral centre adjacent the substituent $R^{33}$ has S stereochemistry and/or the chiral centre adjacent the substituent $R^{32}$ has R stereochemistry are preferred.

Preferably a hydrocarbon chain represented by $A^3$ is a $C_{1-2}$-alkane diyl group, most preferably a methane-diyl group;

$R^{31}$ represents a hydrogen atom or a $C_{1-4}$ alkyl, phenyl, thienyl, benzyl, acetyl or benzoyl group;

$R^{32}$ represents a $C_{3-6}$ alkyl (for example isobutyl) group;

$R^{33}$ represents a benzyl or 4-($C_{1-6}$)alkoxyphenyl-methyl or benzyloxybenzyl group;

$R^{34}$ represents a $C_{1-4}$ alkyl (for example methyl) group; and $R^{35}$ represents a hydrogen atom.

Most preferably the MMPI is selected from batimastat [(2R-(1(S*), 2R*,3S*))-N4-hydroxy-N1-(2-(methylamino)-2-oxo-1-(phenylmethypethyl)-2-(2-methylpropyl)-3-((thienylthio)methyl)butanediamide] and marimastat.

Preferably the MMPI should be present in an amount in the range 1 to 1000 µg, preferably in the range 10 to 150 µg per stent.

Synthesis of compounds of the general formula XI is described in U.S. Pat. No. 5,240,958. Batimastat itself is synthesised in Example 2 of that document.

The stent may be made of a shape memory metal, or may be elastically self-expanding, for instance, be a braided stent. However, preferably it is a balloon expandable stent. In the preferred embodiment of the invention, in which a topcoat is provided, the topcoat may be part of a coherent coating formed over both a stent and a stent delivery device, for instance a balloon of a balloon catheter from which a balloon expandable stent is delivered. In this case, the balloon may additionally be provided with a coating comprising MMPI, for instance adsorbed onto parts of its exterior surface between stent struts. Such a device may be produced by loading the stent with MMPI after the stent has been mounted onto the delivery catheter.

According to a further aspect of the invention there is provided a new method for producing a drug coated intravascular stent comprising the steps:

a) a metallic stent body is coated on its inner and outer walls with a cross-linkable amphiphilic polymer;

b) the cross-linkable polymer is subjected to conditions under which cross-linking takes place to produce a polymer-coated stent;

c) at least the outer coated wall of the polymer coated stent is contacted with liquid drug composition comprising a sparingly water-soluble matrix metalloproteinase inhibitor (MMPI) and an organic solvent in which the MMPI is at least partially dissolved and which is capable of swelling the cross-linked polymer of the coating, for a time sufficient to swell the polymer coating on the outer wall, to produce a wet drug-coated stent;

d) organic solvent is evaporated from the wet stent to produce a dry drug-coated stent.

In the method of the invention, in step c), the MMPI May be both absorbed into the polymer and adsorbed at the process of the polymer coating whereby, upon evaporation of the solvent in step d) crystals of MMPI are formed which are adherent to the surface of the dry drug coated stent.

Alternative substantially all the drug may be absorbed into the polymer, or any surface drug may be rinsed off.

In the method of the invention, contact of the polymer coated stent with the liquid MMPI composition may be by dipping the stent into a body of the stent, and/or by flowing, spraying or dripping liquid composition onto the stent with immediate evaporation of solvent from the wet stent. Such steps allow good control of drug loading onto the stent, and are particularly useful for forming the crystals of drug at the surface of polymer.

Whilst the stent may be provided with drug coating in the invention prior to being mounted onto its delivery device, it is preferred, and most convenient, for the stent to be pre-mounted onto its delivery device prior to carrying out step c). By this means, it is primarily the outer wall of the stent (as opposed to the inner wall of the stent) which becomes coated with MMPI. Whilst this method will generally result in MMPI being coated onto the stent delivery section of the delivery catheter, this is usually, not disadvantageous. In some circumstances it may indeed be useful for the outer surface of the delivery catheter to be provided with a coating of MMPI, which may be delivered to adjacent tissue upon placement of the stent in use. Generally the delivery catheter is in contact with such tissue for a short period, whereby contact is not maintained for a prolonged period, and limited level of transfer of drug from the balloon takes place.

The method of the invention may include a step of applying a topcoat. In such a method a further step e) is carried out:

e) to at least the outer wall of the dry drug coated stent a polymer is applied, to form a non-biodegradable, biocompatible, semi-permeable polymer-containing top-coat.

In this preferred embodiment, in step e) it is preferred that a liquid top-coating composition comprising polymer is coated onto at least the outer wall and is cured after coating to form the top-coat. It is desirable for the liquid coating to be sprayed onto the outer wall of the stent, as this method has been found to minimise removal of previously applied MMPI.

The top-coating composition, and consequently the top coat in the product, should generally be substantially free of MMPI. Preferably it is substantially free of other pharmaceutical actives although in certain circumstances it may be useful to cocoat a mixture of polymer and another pharmaceutically active agent.

For the embodiment of the invention where the liquid top-coating composition comprises a cross-linkable polymer of the type preferred for use to form the first amphiphilic polymer, the liquid top-coating composition comprises crosslinkable polymer and the curing step in the preferred method involves exposure of the top-coat to crosslinking conditions.

Curing of crosslinkable polymer may involve exposure to irradiation, chemical curing agents, catalysts or, more usually raised temperature and/or reduced pressure to acceptable condensation based cross-linking reactions. Drying the liquid during composition usually involves raised temperature and/or reduced pressure for a time sufficient to reduce the amount of solvent remaining on the stent to undetectable levels or levels at which it will not interfere with subsequent processing steps, or with release of the drug in use, or be toxic to a patient in whom the stent is implanted.

Where in the preferred method, the stent is preloaded onto its delivery device before being coated with MMPI, the top-coat is provided over both the stent and the stent delivery section of the delivery catheter. Preferably the top-coat forms a coherent film covering the entire stent delivery section. It is preferred for the device subsequently to be sterilised and to be packaged into a sterile package for storage prior to use. Sterilisation may involve y irradiation, or application of heat, but preferably involves contact with ethylene oxide. We have established, as shown in the worked examples below, that ethylene oxide treatment following loading of drug results in retention of the MMPI compound in a form in which it is indistinguishable, chromatographically, from starting MMPI. It is assumed that the compound is not chemically modified and will have the same biological activity as the starting MMPI applied to the stent.

Where, in the preferred method, a stent is contacted with liquid drug composition whilst mounted on a delivery device, it is important to ensure that the said contact does not adversely effect the properties of the delivery catheter. For a balloon catheter, the contact must not significantly reduce the burst strength of the balloon. A preferred balloon catheter used for delivering a stent is formed of polyamide. We have established that contact of the balloon with ethanol, methanol or dimethylsulfoxide (DMSO) does not damage the balloon such that burst strength is reduced to an unacceptable level.

The solvent used in the liquid drug composition must be selected to allow adequate dissolution of MMPI, and to swell the crosslinked polymer coating to allow absorption of MMPI into the body of the polymer. MMPI which is absorbed into the polymer will be released over a period of time after implantation of the stent. The liquid drug composition may comprise other components, such as crystal modifiers, polymers, salts, acids, bases etc. It may be convenient to include dissolved amphiphilic, optionally crosslinkable polymer, to confer compatibility with the polymer on the stent surface. Such a polymer may be identical to that described above used in the first aspect of the invention.

BRIEF DESCRIPTION OF THE DRAWINGS

FIG. 3 compares the fluorescence spectra of pyrene in lauryl methacrylate and water;

FIG. 4 compares the fluorescence spectra of pyrene in water and in two amphiphilic polymers (Ref Ex 1)

FIG. 5 shows the actual and theoretical release rates of dexamethasone from polymers (Ref Ex 2)

FIG. 6 shows the elution rate for batimastat from polymer coated and uncoated stents release rate from the polymers based on its water solubility (Example 1.1.2).

FIGS. 8 $a$-$d$, 9 $a$-$d$ and 10 $a$-$d$ show the results of example 3; and

DETAILED DESCRIPTION OF THE INVENTION

The present inventors have established that stents according to the invention confer improved quantitative coronary angioplasty results when used in animals, as compared to control polymer coated stents and that the stent is clinically useful in human trials.

The present invention is illustrated in the accompanying examples:

REFERENCE EXAMPLE 1

Zwitterionic polymer coatings were investigated by allowing pyrene to diffuse into the polymer and studying the degree to which it is taken up, and the effects on the ratio of the fluorescence band intensities to see if there is any significant indication of the type of environment present.

Polymer coatings of interest were dissolved in an appropriate solvent (usually ethanol) at 20 mg/ml$^{-1}$, The solution was used to coat polymethylmethacrylate (PMMA) fluorescence cuvettes by simply pouring into the cuvette, draining, following by an oven curing at 70° C. overnight. Polymers studied were:

a) a copolymer of 2-methacryloyloxy ethyl-2'-trimethyl-ammoniumethyl phosphate inner salt (MPC):n-butylmethacrylate:hydroxypropyl methacrylate (HPM):trimethoxysilylpropylmethacylate (TSM) 29:51:15:5 (by weight)

b) a copolymer of MPC:benzylacrylate:HPM:TSM 29:51:15:5 c) a copolymer of MPC:dodecylmethacrylate (DM):HPM:TSM:45:35:15:5 d) a copolymer of MPC:DM:HPM:TSM:29:51:15:5
e) a copolymer of MPC:DM:HPM:TSM:15:65:15:5
f) poly(2-hydroxyethylmethacrylate).

The copolymers a-e were synthesised as disclosed in WO-A 9830615.

Analytical grade pyrene was used in high purity water ($8.32\times10^{-4}$ M). The fluorescence spectrum was recorded using an excitation wavelength of 335 nm and scanned from 350-440 nm on a PE LS 50B Luminescence Spectrophotometer. Subtraction of the spectrum of each coating in water was necessary to remove the interference of a small band at 380 nm present in all methacrylate systems.

Environment information could be obtained by comparing the ratio of the intensity of the peaks at 373 nm (I1) and 383 nm (I3) (I3/I1). Where I3/I1 was similar for polymer systems, the comparative amount of pyrene present could be estimated by the maximum intensity of I1; alternatively, the entire peak area may offer an alternative measure of the comparative amount of pyrene present in different coatings. It was important to mark the side of the cuvette to ensure the same orientations was achieved each time it was replaced in the spectrophotometer.

Figure 1:
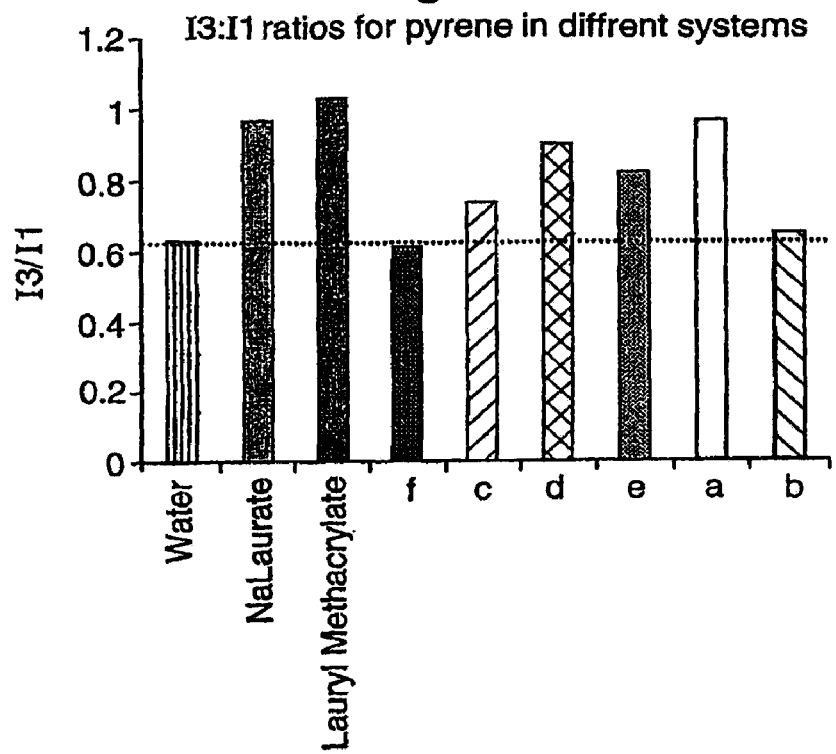
FIG. 1 compares the I3:I1 ratio from the fluorescence spectra of pyrene in different environments (Ref Ex. 1)

FIG. 1 compares the fluorescence spectra of pyrene in lauryl methaciylate (dodecyl methacrylate) ($8.32\times10^{-4}$ M) and water ($8.32\times$M). For water the I3/I1 ratio is 0.633 (literature value 0.63) and the I3/I1 ratio for lauryl methacrylate is 1.029. This indicates the very different environments than might be expected to be seen within the polymer coating.

Figure 2:
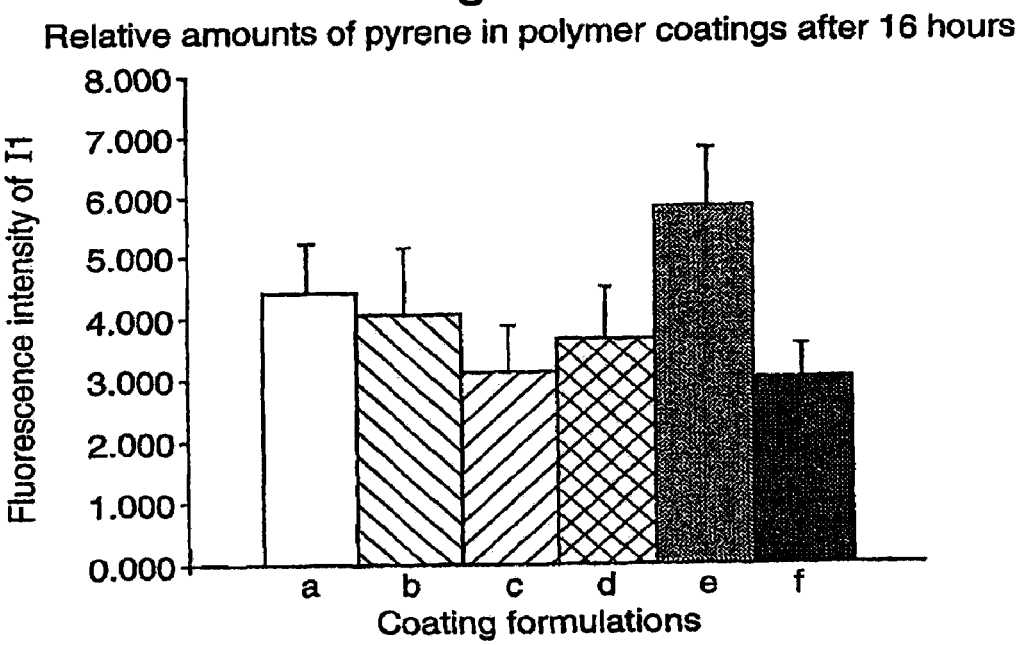
FIG. 2 shows the amount of pyrene retained in a variety of polymer coatings as determined in Reference Example 1.

Pyrene solution added to the coated cuvettes was allowed to stand for 16 h, the cuvette emptied and washed thoroughly with ultrapure water, refilled with ultrapure water and the fluorescence spectrum recorded. The comparative maximum height of I1 was used to estimate the relative amounts of pyrene in the coatings. This was repeated for three cuvettes of each polymer and the average taken. Despite some variations between cuvettes, the trends were the same, indicating that the polymer formulations with more hydrophobic content seemed to contain more pyrene (FIG. 2). This is in contradiction to the water contents of these materials which vary in the opposite order. Hence for the varying systems, although water contents vary in the order c>d>f>e (88:40:38:27), the final fluorescence intensity (loading of pyrene achieved in the coating) varies according to e>d>c≧f. This indicates that the pyrene is preferentially associating itself with hydrophobic areas within the coating.

The ratio of I3/I1 was also studied (FIG. 3) and again, those polymer with formal hydrophobic chains showed a greater ratio (indicating more hydrophobic environment for the pyrene). This polymer containing the benzyl side chain has a lower than expected I3/I1, initially indicating poor interaction with the pyrene. However, measurement of the I3/I1 for pyrene in the pure benzyl acrylate monomer showed that the maximum I3/I1 that could be expected would be 0.75 (i.e. less of a shift in fluorescent intensity is produced in this aromatic monomer compared to the lauryl monomer). PHEMA coating showed I3/I1 characteristic of pyrene in an aqueous environment (FIG. 4), suggesting no formal hydrophobic domain exists.

REFERENCE EXAMPLE 2

Drug-Polymer Interaction Versus Drug Solubility

There are examples of stent-based release of therapeutics that rely upon the poor solubility of the active agent in water to achieve a slow release rate, i.e. by relying for extended release of drug on poor solubility of the drug in water. When a graph of solubility versus release time (T90%) is plotted however, the relationship is extremely poor ($R^2=0.006$) indicating the solubility on its own does not account for the observed release characteristics.

This can be modelled further by comparing the theoretical release of drug into a known volume of water based purely upon its solubility and comparing this with its actual release profile from the polymer system into the same elution volume. Assuming that 100 μg of the drug is place on a surface, and that the drug is eluted off into 5 ml of solution, and then at various arbitrary points, 1 ml removed, and 1 ml of fresh solution added, the dissolution profiles for various drugs could be calculated and compared to experimental data obtained the same way. The variation between calculated and observed could be attributed to the interaction with the polymer matrix.

This is clearly illustrated by FIG. 4. Here, the theoretical release of dexamethasone (which has a log P where P is the partition coefficients of 2.55) has been calculated and plotted on the graph (circles) based on the solubility of the compound and the volume of water into which it is being eluted. The difference between this line and the observed data (squares) is the degree of interaction of the compound with the hydrophobic domains within the polymer coating which in this case is polymer d) from Ref. Example 1. It is the interaction that prolongs the release of the compound and offers some capability to control the delivery of the drug to its surrounding environment.

EXAMPLE 1

1.1.1 Drug Uptake Studies

The solubility of batimastat was tested in ethanol (100%) prior to stent loading investigations. This was by preparation of a series of solutions outlined in Table 1

TABLE 1

Solubility of Batimastat in Ethanol

| Batimastat Concentration in ethanol (100%)/mg per ml | Solubility |
| --- | --- |
| 2.6 | white suspension |
| 1.13 | fine suspension |
| 1.05 | clear suspension |

BiodivYsio DD stents provided with a cross-linked coating on both inner and outer walls of copolymer d) used in Reference Example 1 were provided with a coating of drug in the following manner:

1) Stents were immersed in the drug solution for 5 minutes.
2) Stents were removed from the solution and wick dried on tissue.
3) The stents were allowed to dry for at least 1 hour at room temperature.

DD stents were loaded for 5 minutes. The drug total loading was measured by HPLC, see section 1.2.3. Non-polymer coated stents were tested as controls. The results are shown in section 1.2.1.

1.1.2 Batimastat Elution Studies at 25° C. and 37° C.—Non Flow System

Elution studies were carried out at 25° C. for up to 1 hour in gently agitated PBS. This was done by placing DD stents loaded with batimastat, from section 1.1.1, individually in vials containing 5 ml phosphate buffered saline (PBS) on rollers. At various time intervals a I ml aliquot was removed and replaced with 1 ml fresh PBS. The stents and water aliquots were measured, see section 1.1.4, to give the amount of drug eluted and the amount of drug remaining on the stents, see section 1.2.1 for results.

1.1.3 Elution Studies in Flow-System

Next, the elution of batimastat was examined in a flow system at 37° C. and evaluated over a 2 day period using the best loading conditions. PBS was maintained at 37° C. in six stirred reservoirs (500 ml each) within a water bath. A length of silicone tubing (3 mm internal diameter) was attached from each reservoir to one of six stent chambers (4 mm internal diameter 80 mm long) and back to the respective reservoir via a peristaltic pump. The system was pumped using a flow rate of 100 ml/min to reach equilibrium temperature of 37° C. The flow was stopped and two batimastat loaded stents were placed in each of the six stent chambers, and flow recommenced. A stent was then removed at various time periods and wick dried. These were used to measure the amount of batimastat remaining on the stent. This was continued over a 48 hour period. See section 1.2.3 for results.

1.1.4 Analytical Determination of Drug Loading on DD Stents and Drug Eluted

The following method conditions were used for the HPLC analysis of batimastat:

| | |
|---|---|
| Mobile Phase | Methanol: Water 65.35 (v/v) + 0.15% TFA |
| Column | Phemomenex Luna C8, 250 cm × 6 mm × 3 μm |
| Flow Rate | 0.8 ml/min |
| Detection | UV @ 214 nm |
| Injection Volume | 100 μL |
| Run Time | 8 minutes |

104.5 mg batimastat was placed in a 100 ml flask and dissolved in methanol to give a 1045 ppm stock solution. The batimastat stock solution was serially diluted to give solutions with the nominal concentrations of 10.45, 5.23, 1.05, 0.52, 0.11, 0.05 and 0.01 ppm. All solutions were made up to volume with the mobile phase.

The linearity to of the system was tested by injecting each solution twice and a diluent blank. The repeatability of the system was tested by injecting the 10.45, 1.45 and 0.11 ppm solutions 6 times.

To determine the total loading on DD stents, one stent was placed in 3.0 ml of mobile phase and sonicated for 1 hour. The resulting solution was made up to 5.0 ml with mobile phase and the resulting solution injected onto the system.

Samples of eluent from elution studies were injected directly into the system. The sensitivity of the method was 0.010 ppm (0.010 μg/ml).

1.1.5 Assessment of Changing Solvent on DD Stent Delivery System

In order to load the pre-mounted (on a balloon delivery catheter) DD stent with batimastat, the stent/delivery system combination must be immersed in the drug solution. The aim of this experiment was to check if the solvent had a detrimental effect on the balloons. Pre-mounted BioDivYsio stents were placed in solvent for minutes then allowed to air dry for 47 minutes. The mechanical properties of the balloon were then assessed by a burst pressure test.

The samples were connected to a pressure pump and gauge and a positive pressure of 1 atm. ($10^5$ Pa) applied and left for 30 seconds. The pressure was increased by 1 atm ($10^5$ Pa) every 30 seconds until the stent was fully deployed i.e. there were no creases or folds in the balloon.

The pressure was then increased to 16 atm. ($16 \times 10^5$ Pa) which is the rated burst pressure for the balloon system, and held for 30 seconds. The pressure was then increased in 1 atm.

steps and held for 30 seconds at each step, until the balloon burst. The results are in section 1.2.4.

1.1.6 Batimastat Uptake on Balloon Pre-Mounted DD Stents

Using the optimum loading conditions, see section 1.2.1, a loading trial was carried out on balloon mounted stents in preparation for implant studies in pigs.

The pre-mounted stent was unsheathed and loaded for 5 minutes in 1 ml of 6 mg/ml batimastat in methanol, from a 1 ml syringe. The loaded syringe was pushed onto the pre-cut catheter hoop to immerse the premounted stent, ensuring the whole stent was immersed. After 5 minutes the syringe was removed and the stent allowed to dry for 5 minutes at room temperature. The balloon was then inflated slowly, and the stent removed. For drug uptake results see section 1.2.5.

1.2 Results

1.2.1 Drug Uptake on PC Coated Stents

The amount of batimastat on the 15 mm DD stents were measured after loading for 5 minutes, see Table 2.

TABLE 2

Drug Uptake on PC Coated Stents and Uncoated Stents

| Batimastat Concentration/ mg per ml | Batimastat Drug Solvent | Coating | Total Loading/μg per Stent (no. of stents measured) |
|---|---|---|---|
| 1.05 | Ethanol | Yes | 5.4 ± 0.6(3) |
| 6.03 | Methanol | Yes | 35.1 ± 2.1(3) |
| 50.0 | DMSO/EtOH 90:10 | Yes | 193.1 ± 13.2(3) |
| 10.0 | DMSO/EtOH 10:90 | Yes | 43.3 ± 0.7(3) |
| 10.0 | DMSO/EtOH 10:90 | None | 39.8 ± (3) |
| 10.0 | DMSO/EtOH 10:90 | None | 49.9 ± 7.1(3) |

Loading from ethanol resulted in only a small amount of uptake of batimastat onto the stents. From previous experience increasing the drug loading concentration increased drug uptake. Since ethanol was used as its highest concentration then alternative solvents were required.

Methanol showed a good increase, however a loading greater then 50 μg per stent is preferred. Examination by Scanning Electron Microscopy (SEM) showed good coverage of the stent with single fibre batimastat crystals on the surface.

A combination of 90:10 DMSO and ethanol was tried, which resulted in a very large increase in drug loading. However SEM showed gross webbing of the drug between the stent struts as a mesh of fibres. Reducing the concentration to 30 and 10 mg/ml did not reduce the amount of webbing.

To overcome this level of DMSO was reduced to reduce the amount of webbing and improve the rate of drying since DMSO evaporates more slowly than ethanol at room temperature. 10 mg/ml batimastat in 10:90 DMSO/ethanol gave good packing of the drug on the stent without webbing.

The drug was more tightly packed and structured as crystals with many tendrils compared to the single fibres when loaded from methanol.

Uncoated stents gave an uptake of 40 μg per stent which is equivalent to PC1036 coated stents loaded under the same solvent conditions. The drug was also observed by SEM on the uncoated stents.

To reduce the amount of excess drug crystallised on the coating surface a wash step was included in the loading process. Unmounted stents were loaded as described in section 5.1 from 6 mg/ml batimastat in methanol. After loading one set of stents was dipped in methanol for 5 seconds before drying and a second set after drying, see Table 3. This suggests the washing process was too rigorous, removing all the drug, not just the excess.

TABLE 3

Effect of Wash Step on Drug Loading

| Loading Process | Total Loading/µg per Stent (no. of stents measured) |
|---|---|
| Standard | 35.1 ± 2.1 (3) |
| Pre Drying Wash | 0.1 ± 0.03 (3) |
| Post Drying Wash | 0.1 ± 0.1 (3) |

1.2.2 Drug Elution Studies

The elution of batimastat from 3 stents loaded for 5 minutes in 1.05 mg/ml batimastat in ethanol was measured over 15 minutes at room temperature in PBS, see FIG. 6 for results.

Due to poor total loading from ethanol, the elution of drug was measured over an extended period using stents loaded from methanol, see FIG. 6. Batimastat showed good controlled release over 1 hour. The rate of elution was not restricted by the 5 ml into which the drug was eluted since the amount of drug measured per time point in PBS continued to increase. Only 70% of the drug was accounted for after elution when loaded from methanol. Based on the total amount loaded, 44% of batimastat remained on the stents after 1 hour.

From section 1.2.1 better loading was obtained using 10 mg/ml DMSO/ethanol 10:90. It was noted that uncoated stents gave equivalent drug uptake to coated stents. Therefore the elution of uncoated stents loaded from 10 mg/ml batimastat in DMSO/ethanol 10:90 was measured over 15 minutes, leaving 80% batimastat on the stents. Therefore the elution from both coated and uncoated stents was measured over a longer time span to determine the benefit of the PC polymer.

Figure 7:
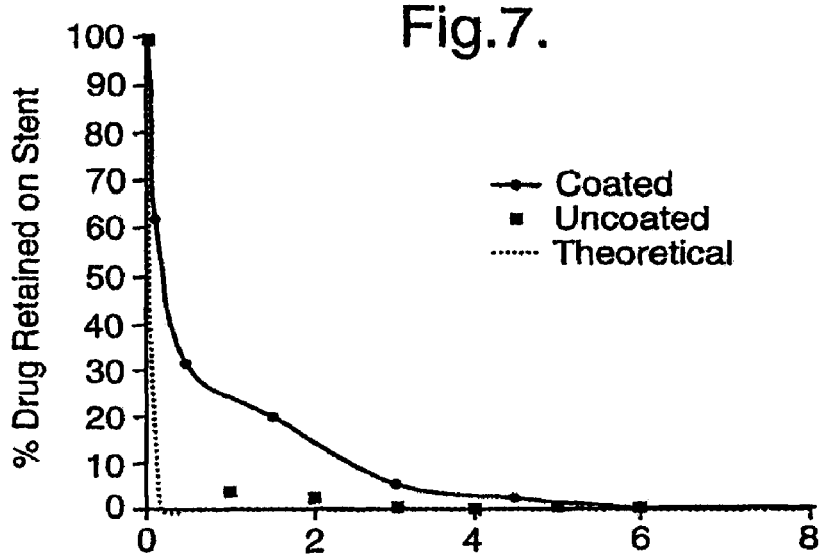
FIG. 7 shows the elution rate of batimastat in a flow model from different systems compared to the theoretical rate (Example 1.1.5).

1.2.3 Elution in Flow Model 10 mg/ml batimastat in DMSO/ethanol 10:90 gave slightly better loading than methanol therefore these were placed in the flow model at 37° C., see FIG. 7. The drug released steadily over 6 hours at 37° C. After 6 hours more than 99% of the batimastat had eluted from the stent. This experiment was repeated on uncoated stents. FIG. 7 shows that 98% batimastat eluted from the stents in 1 hour.

The initial 1 hour elution profile of the coated stent is similar to the uncoated, FIGS. 6 & 7. This may be due to the elution of excess drug on the surface as observed by SEM and the prolonged elution being a result of release of drug entrapped in the coating. The profile in File 7 shows the theoretical release, which would be expected if there was no interaction with the polymer. The fact that this is faster than the actual indicates that there is an interaction. This is believed to be due to hydrophobic interactions between the hydrophobic batimastat molecules and the domains illustrated by the pyrene fluorescence fast described in Reference Example 1.

In vivo, the elution of batimastat from the stents may be slower than indicated in this experiment due to the physical presence of the vessel wall. A concentration gradient may be set up between the drug in the stent and in the vessel wall which may also slow the rate of elution.

1.2.4 Balloon Burst Test Results

Three pre-mounted BioDivYsio stents were assessed in methanol and DMSO, see Table 4.

TABLE 4

Effect of Drug Loading Solvent on Balloon Burst Pressure

| Solvent | Deployment Pressure/atm. | Burst Pressure/atm. |
|---|---|---|
| None | 3 | >16 |
| Ethanol | 3 | >16 |
| Methanol | 3 | 23 ± 1 |
| DMS0 | 3 | 24 ± 1 |

Neither solvent causes detrimental effects on the balloon. The choice of drug loading solvent is therefore related to drying rate and solvent toxicity.

1.2.5 Uptake of Batimastat on Balloon Pre-Mounted Stents

The amount of batimastat on the 18 mm pre-mounted stents was measured after inflation, see Table 5 for results. The stents were loaded from a 6 mg/ml batimastat in methanol solution.

TABLE 5

Batimastat on Expanded Pre-Mounted DD Stents

| | | Total Loading | |
|---|---|---|---|
| Drug Loading time/minutes | Loading Conditions | /µg per stent (no. of stents measured) | /µg per balloon (no. of balloons measured) |
| 5 | Standard | 24.6 ± 10.1 (3) | 23.2 ± 1.2 (3) |
| 5 | Loaded Twice | 20.1 ± 1.2 (3) | 45.6 ± 12.7 (3) |
| 30 | Longer Loading | 23.2 ± 8.8 (3) | 19.2 ± 1.9 (3) |
| 5 | Additional 2 × 15 ul Drops | 108.5 ± 6.0 (3) | 126.7 ± 32.6 (3) |

Using standard loading conditions gave loading similar to unmounted stents, see Table 2. To increase this several trials were made, firstly by repeating the loading process after initial loading, and secondly trying an increase in loading time of 30 minutes. Neither showed an increase in drug uptake, see Table 5.

Next additional loading solution was applied as droplet after the standard loading process, this way the drug could not redissolve from the stent. Using a micro-line pipette (Gilson type) a 15 µl aliquot of the drug loading solution was placed onto the stent. The drop of drug solution was spread along the stent. The stent was allowed to dry for 1 minute, then repeated with 15 µl to give a total addition of 30 µl.

The increased loading was equivalent to the amount of drug added as drops, shared equally between the stent and balloon, see Table 5.

1.3 Conclusions

The coat loading of batimastat on PC polymer coated stents was improved by using higher concentration of drug in the liquid compositions. This, in turn, requires changing from ethanol to either methanol or a combination of DMSO and ethanol, in which batimastat is more soluble.

The elution of batimastat was at a controlled rate, with 99% being removed from the stent after 6 hours at 37° C., in the flow system. This performance matches predictions from the value for the partition coefficient. Batimastat has a calculated log P of 2.45.

EXAMPLE 2

Effects of Sterilisation

Stents provided with one top-coating layer (formed by applying a solution of polymer d) in ethanol to the drug loaded stent mounted on a balloon stent delivery catheter) were subjected to ethylene oxide' treatment, under sterilisation conditions. Subsequently the ethylene oxide treated stent and non-ethylene oxide treated stents were tested for the level of drug after inflation, using the general technique of Example 1.1.4 and using HPLC, 1H and $^{13}$C NMR and polarimetry. The results indicate that the level of drug detected by this method for the post ethylene oxide treated product was not significantly different from the pre-treated product. The HPLC, NMR and polarimetry results indicate that the batimastat has not been adversely affected by the ethylene oxide treatment.

EXAMPLE 3

Re-Endothelialisation of Batimastat-Loaded BiodivYsio Stents

BiodivYsio stents (control, low dose batimastat and high dose batimastat) were implanted into healthy farm swine. After 5 days the animals were sacrificed and the stents studied for endothelialisation using scanning electron microscopy. It was found that batimastat-loaded onto 15 mm BiodivYsio stents at either low or high dose concentrations, 34.2±1.6 and 115.3±16.1 µg batimastat per stent (equivalent to 0.43±0.02 and 1.43±0.20 µg per mm$^2$ of stent) respectively, did not affect the endothelialisation process in-vivo at 5 days. The drug-loaded stents showed continuous and confluent layers of endothelia and were comparable to the control stents without drug.

The stents were implanted into the coronary arteries of farm swine (2 per animal, each in different arteries). After sacrifice, the vessels were excised and trimmed of all extraneous tissue, washed in buffer, and fixed in 2.5% glutaraldehyde at pH 7.4. Fixation was carried out for a minimum of 24-48 hours in 2.5% glutaraldehyde. The section of artery was rinsed in 0.1 M cacodylate buffer pH 7.4. The arteries were shipped in 0.1 M cacodylate buffer pH 7. The vessels were required to be left whole, i.e. without longitudinal transection. A small V was marked in the proximal end of the vessel to determine vessel orientation. SEM analysis was carried out on three sections of the stented artery and at 2 different magnifications (high and low). The analysis concentrated on the rate and extent of re-endothelisation of the stent struts and the presence of any cellular/biological debris within the stented segment of artery.

Some typical results for control, low dose and high dose stents are shown in FIGS. 8-10.

FIGS. 8a-8d show SEM results from the control stent (polymer coated, no drug).

FIG. 8 is a 13× magnification of the distant end (relative to the surgeon) of the stated vessel which FIG. 8b is a 13× magnification of the proximal end of the stented vessel. FIG. 8c is a 259 times magnification of the luminal surface proximal to the stent and FIG. 8d is a similar area at 2190× magnification which shows endothelial and some white blood cells.

FIG. 9a-d show SEM results for the low dose batimastat loaded stent. FIGS. 9a and 9b correspond to FIGS. 8a and b, respectively at the same magnification. FIG. 9c shows the luminal surface proximal to stent at 135 times and FIG. 9d is a higher magnification (1800×) of the same area.

FIG. 10a-d show SEM results for the high dose batimastat loaded stent. FIGS. 10a and b corresponds to and are at the same magnification as FIG. 8a and b, respectively. FIG. 10c shows the endothetial surface between the struts at the proximal end at 320× magnification and FIG. 10d shows the same area at 2150× magnification, showing white blood cells and a macrophage on endothelial cells.

EXAMPLE 4

Pharmacokinetic Study (PK)

The pharmacokinetic studies were initiated to investigate the deposition of drug from the batimastat-loaded BiodivYsio stent. These studies used the well established New Zealand white rabbit model where $^{14}$C batimastat-loaded BiodivYsio stents were placed in the left and right iliac arteries and levels of batimastat deposited in the iliac arteries and solid organs were measured twenty eight days after stent implantation.

The study demonstrated the reproducible release and deposition of drug from the BiodivYsio Batimastat stent. First order release was observed such that the bulk of loaded drug (94%) was eluted 28 days post-implantation. Drug released from each stent was primarily localized to the 15 mm long stented region, and to a lesser degree the adjacent adventitia, and regions immediately proximal and distal to the stent. The data followed the expected patterns of release and deposition and indicated that there is unlikely to be any long term issue of residual drug within the arterial wall after release is complete.

Very little of the drug was found in the distal organs (brain, liver, kidney, spleen, carotid artery, gonad, heart, lung, and intestine), the numbers detected being so low they were considered to be within the background noise level of the assay, and for all intents and purposes to be considered as undetectable.

EXAMPLE 5

One-Month Pre-Clinical Assessment in Farm Swine

A total of 24 stents were implanted in 12 farm swine pigs for 1 month. Two doses were assessed: 0.30±013 µg batimastat per mm$^2$ of stent surface area, was obtained using a dip loading process prior to implantation; the higher dose of 1.09±0.06 µg batimastat per mm$^2$ of stent, was obtained using an additional loading process. The higher dose was set at the maximum quantity that could be loaded onto the stent. Analysis of the Quantitative Coronary Angiogram (QCA) and histomorphometric results show that there was a significant difference between the intimal area for the low dose of batimastat compared to the control (2.5 vs 4.0). Histological examination confirmed that all the vessels were patent, without the presence of thrombus in the vessel lumen. All sections showed stent struts to be completely covered, leading to a smooth endoluminal surface. There was no excessive inflammatory response at stent struts in BiodivYsio Batimastat treated sections compared to the control sections. Medial and adventitial layers appeared similar in all three groups. The perivascular nerve fibers, the adipose tissue and adjacent myocardium appeared normal in control and BiodivYsio Batimastat treated sections. Therefore this study demonstrated that the BiodivYsio Batimastat stent with low and high dose was well tolerated up to 28 days, low dose demonstrating some anti-restenotic potential.

EXAMPLE 6

3-Month Pre-Clinical Evaluation in Yucatan Minipigs

The 3 month data from a short and longer-term safety study on Yucatan minipigs using two doses of batimastat, 0.03±0.01

(low dose) and 0.30±0.13 μg (high dose) batimastat per mm² of stent showed some efficacy.

In the control group it was found that the stenosis rate was 34% (QCA analysis). After 3 months a trend in favour of the treatment groups was found, with an indication of a dose-response relationship shown in FIG. 5. The stenosis was reduced by 20% and 34% in the low and high dose groups respectively compared to the control. However this difference was not statistically significantly different (p=0.15 ANOVA analysis).

EXAMPLE 7

Batimastat Delivered Per mm² of the Coronary Artery Vessel Wall

Figure 11:
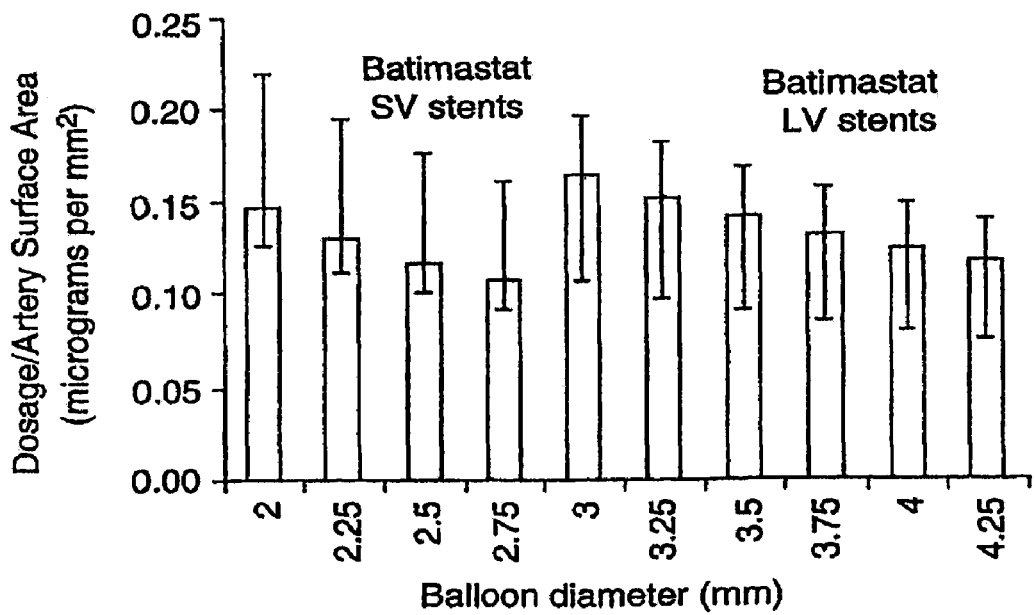
FIG. 11 shows the data explained in example 7.

As the dose per stent is fixed, the quantity of batimastat delivered per mm² of coronary artery vessel wall is dependent upon the diameter of the vessel. The data in FIGS. 11-11c demonstrate the calculated quantity of batimastat that can be delivered per mm² of vessel wall from the BiodivYsio Batimastat LV & SV stents (LV=large vessel 3-4 mm deployed; SV=small vessel 2-3 mm deployed). In the calculation of vessel wall surface area it has been assumed that the vessel wall is a cylinder with a uniform cross-section.

The data show that the mean quantity of batimastat delivered from an 18 mm SV stents is within the range of 0.09-0.22 μg/mm²/vessel wall, which is in line with the mean quantity of batimastat delivered from similar length BiodivYsio LV stent which is within the range of 0.07-0.21 μg/mm²/vessel wall.

EXAMPLE 8

Clinical Trial Assessment—30 Day Data for First 30 Patients

Batimastat anti-restenosis trial utilising the BiodivYsio Local Drug Delivery PC-stent (BRILLIANT-EU) which is a mutli-centre prospective study performed at 3 centres in France and 3 centres in Belgium with 170 patients. The primary objective of this study was to evaluate the occurrence of MACE (death, recurrent myocardial infarction or clinically driven target lesion revascularisation) to 30 days post procedure in patients who received a BiodivYsio batimastat stent. The secondary objectives were to evaluate: Incidence of sub(acute) thrombosis, binary restenosis and other QCA endpoints. 11, 15, 18, 22 and 28 mm BiodivYsio batimastat stents by 3.0 to 4.0 mm in diameter were under investigation.

30 day data for the first 30 patients are reported in this example. Other endpoints have not yet been reached and therefore will not be described.

31 patients (87% male) with an average height of 170 cm and weight of 78 Kg were enrolled into the study. 52% of patients had a history of hypercholesterolaemia and 78% had smoked or were current smokers. 74% of patients had single vessel disease and 32% had a history of previous MI. The vessel/lesion characterisations were as follows:

| Vessel | Treated | Lesion | Classification |
|---|---|---|---|
| RCA | 35% | A | 26% |
| LAD | 48% | B1 | 35% |
| Cx | 9% | B2 | 26% |
| Other | 6% | C | 13% |

The mean lesion length treated was 12 mm. The majority of patients had either a 15 mm (42%) or an 18 mm (29%) stent implanted. The stent was adequately positioned in all patients, there were no cases of delivery balloon rupture or stent embolisation. There were no MACE resulting from the angioplasty or stenting procedure.

At 30 day follow-up one patient had a MACE (patient 12 died 21 days post procedure) and 3 patients had serious adverse events that were unrelated to the study treatment (Table 6).

There were no reported cases of sub(acute) thrombosis.

There were no significant changes in blood parameters either immediately post procedure or at 30 day follow-up (other than those that would be expected as a result of the interventional procedure e.g. elevated CK levels).

Technical device success defined as intended stent successfully implanted as the first stent was 100%. Clinical device success defined as technical device success in the absence of MACE to discharge was also achieved in all patients.

Pharmacokinetic studies have shown that ~95% of the batimastat will have been eluted from the PC coating after 28 days (Example 4). Therefore the data presented in this initial interim analysis suggest that the presence of batimastat in the coating is not associated with an increased occurrence of MACE or serious adverse events and that the BiodivYsio Batimastat stent is safe in the short term for use in patients.

TABLE 6

Patients with Major Adverse Cardiac Events (MACE) - Safety Analysis Set

| Major Adverse Cardiac Event | In Hospital | | Up to 30 days follow-up | |
|---|---|---|---|---|
| | Number (%) of patients | Number of events | Number (%) of patients | Number of events |
| Cardiac death | 0 (0) | 0 | 1 (3) | 1 |
| Q-wave MI | 0 (0) | 0 | 0 (0) | 0 |
| Non Q-wave MI | 0 (0) | 0 | 0 (0) | 0 |
| CABG | 0 (0) | 0 | 0 (0) | 0 |
| Repeat angioplasty | 0 (0) | 0 | 0 (0) | 0 |
| TOTAL | 0 (0) | 0 | 1 (3) | 1 |

The invention claimed is:

1. An intravascular stent comprising a metal body having a coating comprising polymer and a restenosis inhibiting agent in which the restenosis inhibiting agent is a sparingly water soluble matrix metallo-proteinase inhibitor (MMPI) and the polymer in the coating is a cross-linked amphiphilic polymer formed from a crosslinkable polymer of formula IX

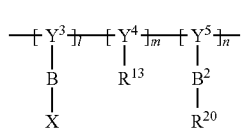

wherein l is 1 to 75, m is 0 to 99, n is 0 to 33 and m+n is 25 to 99,
$Y^3$, $Y^4$, and $Y^5$ are the groups derived from Y, $Y^1$, and $Y^2$ respectively, of the radical initiated addition polymerisation of the ethylenic group in Y, $Y^1$, and $Y^2$, wherein Y, $Y^1$, and $Y^2$ are independently selected from the group consisting of

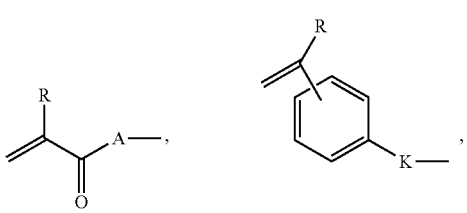

CH$_2$=C(R)CH$_2$O—, CH$_2$=C(R)CH$_2$OC(O)—, CH$_2$=C(R)OC(O)—, CH$_2$=C(R)O—, CH$_2$=C(R)CH$_2$OC(O)N(R$^1$)—, R$^2$OOCCR=CRC(O)O—, RCH=CHC(O)O—, RCH=C(COOR$^2$)CH$_2$C(O)O—,

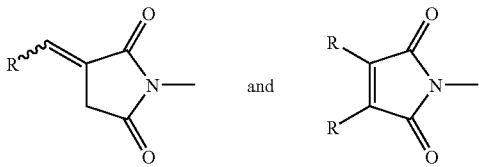

wherein:
R is hydrogen or a C$_1$-C$_4$ alkyl group;
R$^1$ is hydrogen or a C$_1$-C$_4$ alkyl group or R$^1$ is —B—X;
R$^2$ is hydrogen or a C$_{1-4}$ alkyl group;
A is —O— or —NR$^1$—;
K is a group selected from the group consisting of —(CH$_2$)$_p$OC(O)—, —(CH$_2$)$_p$C(O)O—, —(CH$_2$)$_p$OC(O)O—, —(CH$_2$)$_p$NR$^3$—, —(CH$_2$)$_p$NR$^3$C(O)—, —(CH$_2$)$_p$C(O)NR$^3$—, —(CH$_2$)$_p$NR$^3$C(O)O—, —(CH$_2$)$_p$OC(O)NR$^3$—, —(CH$_2$)$_p$NR$^3$C(O)NR$^3$— (in which the groups R$^3$ are the same or different), —(CH$_2$)$_p$O—, —(CH$_2$)$_p$SO$_3$—, or, optionally in combination with B, a valence bond;
p is from 1 to 12;
R$^3$ is hydrogen or a C$_1$-C$_4$, alkyl group;
B is a straight or branched alkylene (alkanediyl), alkyleneoxaalkylene, alkylene oligo-oxaalkylene chain optionally containing one or more fluorine atoms up to and including perfluorinated chains, or a valence bond;
B$^2$ is a straight or branched alkylene, oxaalkylene, oligo-oxaalkylene chain optionally containing one or more fluorine atoms up to and including perfluorinated chains, or a valence bond;
X is a zwitterionic group;
R$^{13}$ is a hydrophobic group; and
R$^{20}$ is a cross-linkable group.

2. The stent according to claim 1 in which on at least the outer wall of the stent the coating comprises a layer of the said amphiphilic polymer in which the MMPI is absorbed.

3. The stent according to claim 1 in which the polymer in the coating when swollen with water containing pyrene has hydrophobic domains observable by an I3:I1 ratio of more than 0.8 preferably about 1.

4. The stent according to claim 1 in which on at least the outer wall of the stent the coating comprises an inner layer of the said amphiphilic polymer, and, adhered to said inner layer, crystalline MMPI.

5. The stent according to claim 1, wherein X has a formula selected from II, IV, and V,

—X$^1$—R$^4$—N$^+$(R$^5$)$_2$—R$^6$—V   II, wherein
X$^1$ is a valence bond, —O—, —S— or —NH—,
V is a carboxylate, sulphonate or phosphate (diester-monovalently charged) anion;
R$^4$ is a valence bond (together with X$^1$), or alkylene —C(O)alkylene-, or —C(O)NHalkylene;
the groups R$^5$ are the same or different and each is hydrogen or alkyl of 1 to 4 carbon atoms or the groups R$^5$ together with the nitrogen to which they are attached form a heterocyclic ring of 5 to 7 atoms; and
R$^6$ is alkylene of 1 to 20;

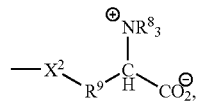

wherein
X$^2$ is a valence bond, —O—, —S— or —NH—,
R$^9$ is a valence bond (optionally together with X$^2$), or alkylene, —C(O)alkylene- or —C(O)NHalkylene; and
the groups R$^8$ are the same or different and each is hydrogen or alkyl of 1 to 4 carbon atoms, or two of the groups R$^8$, together with the nitrogen to which they are attached, form a heterocyclic ring of from 5 to 7 atoms, or the three group R$^8$ together with the nitrogen atom to which they are attached form a fused ring structure containing from 5 to 7 atoms in each ring;

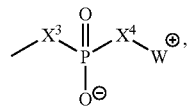

wherein the moieties X$^3$ and X$^4$, which are the same or different, are —O—, —S—, —NH— or a valence bond, and
W+ is a group comprising an ammonium, phosphonium or sulphonium cationic group and a group linking the anionic and cationic moieties.

6. The stent according to claim 5, wherein for formula II:
X$^1$ is —O—;
R$^4$ is C$_1$-C$_6$ alkylene; and
R$^6$ is C$_1$-C$_6$ alkylene;
for formula IV:
X$^2$ is —O—;
the groups R$^8$ are methyl; and
R$^9$ is C$_1$-C$_6$ alkylene;
for formula V:
X$^3$ and X$^4$ are —O—; and
the group linking the anionic and cationic moieties is a C$_{1-12}$-alkanediyl group.

7. The stent according to claim 1, wherein X has a formula V,

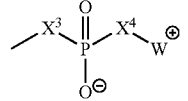

wherein
W contains as cationic group an ammonium group;
the group $W^+$ is selected from the group of formula $-W^1-N^+R^{10}{}_3$, $-W^1-P^+R^{11}{}_3$, $-W^1-S^+R^{11}{}_2$, or $-W^1-Het^+$; wherein
$W^1$ is alkanediyl of 1 or more carbon atoms, optionally containing one or more ethylenically unsaturated double or triple bonds, disubstituted-aryl, alkylene aryl, aryl alkylene, or alkylene aryl alkylene, disubstituted cycloalkyl, alkylene cycloalkyl, cycloalkyl alkylene or alkylene cycloalkyl alkylene, which group $W^1$ optionally contains one or more fluorine substituents and/or one or more functional groups;
either the groups $R^{10}$ are the same or different and each is hydrogen or alkyl of 1 to 4 carbon atoms, preferably methyl, or aryl, or two of the groups $R^{10}$ together with the nitrogen atom to which they are attached form a heterocyclic ring containing from 5 to 7 atoms or the three groups R together with the nitrogen atom to which they are attached form a fused ring structure containing from 5 to 7 atoms in each ring, and optionally one or more of the groups $R^{10}$ is substituted by a hydrophilic functional group,
the groups $R^{11}$ are the same or different and each is $R^{10}$ or a group $OR^{10}$, where $R^{10}$ is as defined above; and
Het is an aromatic nitrogen-, phosphorus-, or sulphur-.

8. The stent according to claim 7, wherein $W^1$ is $C_2$-$C_6$ alkanediyl, aryl group is phenyl, and Het group is pyridinyl.

9. The stent according to claim 7, wherein $W^1$ is ethane-1,2-diyl.

10. The stent according to claim 1, wherein X has a formula of III

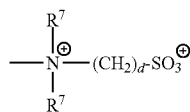

wherein the groups $R^7$ are the same or different and each is hydrogen or $C_{1-4}$ alkyl, and d is from 2 to 4.

11. The stent according to claim 10, wherein the groups $R^7$ are the same.

12. The stent according to claim 10, wherein the groups $R^7$ are both methyl.

13. The stent according to claim 1, wherein X has a formula of VI,

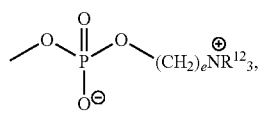

wherein
the groups $R^{12}$ are the same or different and each is hydrogen or $C_{1-4}$ alkyl, and e is from 1 to 4.

14. The stent according to claim 13, wherein the groups $R^{12}$ are the same.

15. The stent according to claim 13, wherein the groups $R^{12}$ are all methyl.

16. The stent according to claim 1, wherein $R^{13}$ is a straight or branched alkyl, alkoxyalkyl or oligoalkoxyalkyl chain containing 4 or more, preferably 6 to 24 carbon atoms, unsubstituted or substituted by one or more fluorine atoms optionally containing one or more carbon double or triple bonds; or a siloxanegroup $-(CR^{18}{}_2)_{qq}(SiR^{19}{}_2)(OSiR^{18}{}_2)_{pp}R^{19}$ in which each group $R^{18}$ is the same or different and is hydrogen or alkyl of 1 to 4 carbon atoms, or aralkyl, for example benzyl or phenethyl, each group $R^{19}$ is alkyl of 1 to 4 carbon atoms, qq is from 1 to 6 and pp is from 0 to 49.

17. The stent according to claim 16, wherein $R^{13}$ is a straight alkyl having 4 to 18 carbon atoms.

18. The stent according to claim 1, wherein $R^{20}$ is selected so as to be reactive with itself or with a functional group in the polymer or at a surface to be coated.

19. The stent according to claim 18, wherein $R^{20}$ is selected from the group consisting of ethylenically and acetylenically unsaturated groups containing one or more radicals; aldehyde groups; silane and siloxane groups, each containing one or more substituents selected from halogen atoms; $C_{1-4}$-alkoxy groups; hydroxyl; amino; carboxyl; epoxy; $-CHOHCH_2Hal$ (in which Hal is selected from chlorine, bromine and iodine atoms); succinimido; tosylate; triflate; imidazole carbonyl amino; optionally substituted triazine groups; acetoxy; mesylate; carbonyl di(cyclo)alkyl carbodiimidoyl; isocyanate; acetoacetoxy; and oximino.

20. The stent according to claim 18, wherein $R^{20}$ comprises a silane group containing at least one substituent selected from halogen atoms and $C_{1-4}$-alkoxy groups.

21. The stent according to claim 1, wherein B and $B^2$ are independently straight chain $C_{2-8}$-alkanediyl.

22. The stent according to claim 1, wherein the polymer has a formula of formula X or a salt thereof,

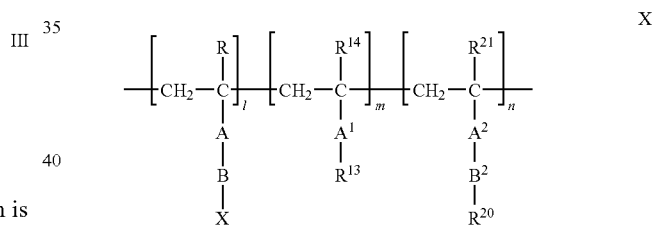

wherein
$R^{14}$ is hydrogen or a $C_1$-$C_4$ alkyl group;
$A^l$ is $-O-$ or $-NR^{15}-$;
$R^{15}$ is hydrogen, a $C_1$-$C_4$ alkyl group or $R^{13}$;
$R^{21}$ is hydrogen or a $C_1$-$C_4$ alkyl group;
$A^2$ is $-O-$ or $-NR^{22}-$;
$R^{22}$ is hydrogen, a $C_1$-$C_4$ alkyl group or $B^2R^{20}$; and
each $R^{20}$ is a independently a cross-linkable group.

23. The stent according to claim 1, wherein the MMPI is a hydroxamic acid based collagenase inhibitor which is an oligopeptide compound of the general formula XI

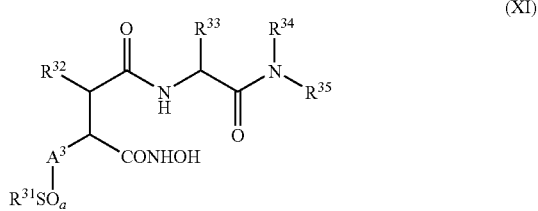

wherein:
a is an integer having the value 0, 1 or 2; and
$R^{31}$ represents a hydrogen atom, $C_{1-6}$ alkyl, phenyl, thienyl, substituted phenyl, phenyl($C_{1-6}$)alkyl, heterocyclyl, ($C_{1-6}$)alkylcarbonyl, phenacyl or substituted phenacyl group; or when a=0, $R^{31}$ represents $R^x$, wherein $R^x$ represents a group:

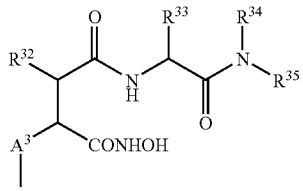

$R^{32}$ represents a hydrogen atom or a $C_{1-6}$ alkyl, $C_{1-6}$ alkenyl, phenyl($C_{1-8}$) alkyl, cycloalkyl(—$C_{1-6}$)alkyl or cycloalkenyl($C_{1-6}$)alkyl group;

$R^{33}$ represents an amino acid side chain or a $C_{1-6}$ alkyl, benzyl, ($C_{1-6}$ alkoxy) benzyl, benzyloxy($C_{1-6}$ alkyl) or benzyloxbenzyl group;

$R^{34}$ represents a hydrogen atom or a methyl group;

$A^3$ represents a $C_{1-6}$ hydrocarbon chain, optionally substituted with one or more $C_{1-6}$ alkyl, phenyl or substituted phenyl groups.

24. The stent according to claim 15, wherein $R^{33}$ represents an amino acid side chain which is a characteristic side chain attached to the —CH(NH$_2$)(COOH) moiety in the following R or S amino acids: glycine, alanine, valine, leucine, isoleucine, phenylalanine, tyrosine, tryptophan, serine, threonine, cysteine, methionine, asparagine, glutamine, lysine, histidine, arginine, glutamic acid and aspartic acid.

25. The stent according to claim 1, wherein the MMPI is batimastat or marimastat.

26. The stent according to claim 1, wherein the MMPI is present in an amount in the range of 1 μg to 1000 μg per stent.

27. A method for producing a drug coated intravascular stent according to claim 1, said method comprising:
a) coating a metallic stent body on its inner and outer walls with the cross-linkable amphiphilic polymer;
b) subjecting the cross-linkable polymer to conditions under which cross-linking takes place to produce a polymer-coated stent;
c) contacting at least the outer coated wall of the polymer coated stent with a liquid drug composition comprising a sparingly water-soluble matrix metalloproteinase inhibitor (MMPI) and an organic solvent in which the MMPI is at least partially dissolved and which is capable of swelling the cross-linked polymer of the coating, for a time sufficient to swell the polymer coating on the outer wall, to produce a wet drug-coated stent; and
d) evaporating the organic solvent from the wet drug-coated stent to produce a dry drug-coated stent.

28. The method according to claim 27, wherein, in step c), the MMPI is both absorbed into the polymer and adsorbed at the surface of the polymer coating, whereby, upon evaporation of the solvent in step d), crystals of the MMPI are formed which are adherent to the surface of the dry drug-coated stent.

29. The method according to claim 27, wherein, in step c), the contacting is by dipping the polymer coated stent in the liquid drug composition, optionally repeatedly dipping.

30. The method according to claim 27, wherein in step c), the contacting is by flowing, spraying or dripping the liquid drug composition onto the stent, and immediately allowing evaporation of the solvent from the wet drug-coated stent in step d).

31. The method according to claim 28, wherein the stent is, between steps b) and c), mounted onto the stent delivery section of a stent-delivery catheter, whereby the stent delivery section is also contacted with the liquid drug composition.

32. The method according to claim 31, wherein the stent-delivery catheter is a balloon catheter in which the balloon is formed of polyamide, and wherein the organic solvent in the liquid drug composition is selected from dimethylsulphoxide, dichloromethane, $C_{1-4}$ alcohol, and admixtures thereof.

33. The stent according to claim 16, wherein $R^{13}$ is a straight alkyl having 12 to 16 carbon atoms.

34. The stent according to claim 1, wherein the MMPI is present in an amount in the range 10 μg to 150 μg per stent.

* * * * *